(12) United States Patent
Shapiro et al.

(10) Patent No.: US 11,908,557 B1
(45) Date of Patent: Feb. 20, 2024

(54) PROGRAMMATICALLY MANAGING SOCIAL DETERMINANTS OF HEALTH TO PROVIDE ELECTRONIC DATA LINKS WITH THIRD PARTY HEALTH RESOURCES

(71) Applicant: UnitedHealth Group Incorporated, Minnetonka, MN (US)

(72) Inventors: Sheila Kay Shapiro, Phoenix, AZ (US); Donna McClure, Phoenix, AZ (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 283 days.

(21) Appl. No.: 16/791,110

(22) Filed: Feb. 14, 2020

Related U.S. Application Data

(60) Provisional application No. 62/805,500, filed on Feb. 14, 2019.

(51) Int. Cl.
*G16H 20/00* (2018.01)
*G16H 15/00* (2018.01)
*G16H 10/60* (2018.01)

(52) U.S. Cl.
CPC ............ *G16H 20/00* (2018.01); *G16H 10/60* (2018.01); *G16H 15/00* (2018.01)

(58) Field of Classification Search
CPC ........ G16H 20/00; G16H 10/60; G16H 15/00; G16H 50/30; G16H 50/70; G16H 50/20; G16H 10/20; G16H 10/40; G16H 50/50; G06N 20/00; G06K 9/62; G06F 15/16; G06F 21/00; G06F 19/3481; G06F 19/3456; A61B 5/00
USPC ........................................................ 705/2, 3
See application file for complete search history.

(56) References Cited

U.S. PATENT DOCUMENTS

| 10,185,809 B1 | 1/2019 | Zhou et al. |
| 2008/0065419 A1* | 3/2008 | Esseiva ............ G16H 10/65 |
| | | 705/3 |

(Continued)

FOREIGN PATENT DOCUMENTS

WO    2015/183828 A1    12/2015

OTHER PUBLICATIONS

Paul A. LaBrec and Ryan Butterfield, "The Development and Application of a Composite Score for Social Determinants of Health", Paper 882-2017 https://files.ama-ihmi.org/image/authenticated/s-4jVzBV1-/The_Development_and_Application_of_a_Composite_Score_for_Social_rezj5f.pdf (Year: 2017).*

(Continued)

*Primary Examiner* — Mamon Obeid
*Assistant Examiner* — Alaaeldin M Elshaer
(74) *Attorney, Agent, or Firm* — Alston & Bird LLP

(57) ABSTRACT

Certain embodiments are directed to systems and methods for automatically providing data indicative of one or more characteristics of services that may be recommended to a particular patient, wherein the services are executable at least in part electronically based on data generated and provided by a system for facilitating access to the services. The generated data may be utilized for generating one or more user interfaces providing data regarding derived standard pricing data that is automatically assigned to the referred services and which may be attributable to a patient based at least in part on the patient's usage of the services.

20 Claims, 17 Drawing Sheets

(56) References Cited

U.S. PATENT DOCUMENTS

| | | | |
|---|---|---|---|
| 2009/0326981 A1 | 12/2009 | Karkanias et al. | |
| 2010/0262837 A1 | 10/2010 | Kulin | |
| 2012/0143013 A1 | 6/2012 | Davis, III et al. | |
| 2012/0192253 A1* | 7/2012 | Betsch | G06F 21/6245 726/4 |
| 2012/0232929 A1 | 9/2012 | Experton | |
| 2018/0053012 A1 | 2/2018 | Myers et al. | |
| 2018/0091413 A1 | 3/2018 | Richards et al. | |
| 2018/0358117 A1 | 12/2018 | Neagle | |
| 2019/0074072 A1 | 3/2019 | Aldridge et al. | |
| 2019/0243911 A1 | 8/2019 | Kobozev et al. | |
| 2021/0174968 A1* | 6/2021 | Butterfield | G06K 9/6247 |

OTHER PUBLICATIONS

Rachel Gold et al. "Developing Electronic Health Record (EHR) Strategies Related to Health Center Patients' Social Determinants of Health" The Journal of the American Board of Family Medicine Jul. 2017, 30 (4) 428-447; DOI: https://doi.org/10.3122/jabfm.2017.04.170046 (Year: 2017).*

"3M All Patient Refined Diagnosis Related Groups (APR DRGs)," 3M Science Applied to Life, (8 pages), (online). [Retrieved from the Internet Feb. 19, 2020] <https://www.3m.com/3M/en_US/health-information-systems-us/providers/grouping-and-classification/apr-drgs/>.

"3M Outpatient Grouping, Editing and Reimbursement Content," 3M Science Applied to Life, 3M Health Information Systems, (3 pages), Oct. 2019.

"Enhanced Patient Matching Is Critical to Achieving Full Promise of Digital Health Records," The Pew Charitable Trusts, (57 pages), Oct. 2, 2018, (online). [Retrieved from the Internet Feb. 19, 2020] <https://www.pewtrusts.org/en/research-and-analysis/reports/2018/10/02/enhanced-patient-matching-critical-to-achieving-full-promise-of-digital-health-records>.

Abouelmehdi, Karim et al. "Big Healthcare Data: Preserving Security and Privacy," Journal of of Big Data, pp. 1-18, Dec. 2018, vol. 5, No. 1. DOI: 10.1186/s40537-017-0110-7.

* cited by examiner

Personal Characteristics

1. Are you Hispanic or Latino?

| Yes | No | I choose not to answer this question |
|---|---|---|
|  |  |  |

2. Which race(s) are you? Check all that apply.

| Asian | Native Hawaiian |
|---|---|
| Pacific Islander | Black/African American |
| White | American Indian/Alaskan Native |
| Other (please write): | |
| I choose not to answer this question | |

3. At any point in the past 2 years, has season or migrant farm work been your or your family's main source of income?

| Yes | No | I choose not to answer this question |
|---|---|---|
|  |  |  |

4. Have you been discharged from the armed forces of the United States?

| Yes | No | I choose not to answer this question |
|---|---|---|
|  |  |  |

5. What language are you most comfortable speaking?

| English |
|---|
| Language other than English (please write) |
| I choose not to answer this question |

Family & Home

6. How many family members, including yourself, do you currently live with? _____

| I choose not to answer this question |
|---|

7. What is your housing situation today?

| I have housing |
|---|
| I do not have housing (staying with others, in a hotel, in a shelter, living outside on the street, on a beach, in a car, or in a park) |
| I choose not to answer this question |

8. Are you worried about losing your housing?

| Yes | No | I choose not to answer this question |
|---|---|---|
|  |  |  |

9. What address do you live at?

Street: _____
City, State, Zipcode: _____

Money & Resources

10. What is the highest level of school that you have finished?

| Less than high school degree | High school diploma or GED |
|---|---|
| More than high school | I choose not to answer this question |

11. What is your current work situation?

| Unemployed | Part-time or temporary work | Full-time work |
|---|---|---|
| Otherwise unemployed but not seeking work (ex: student, retired, disabled, unpaid primary care giver) Please write: | | |
| I choose not to answer this question | | |

12. What is your main insurance?

| None/uninsured | Medicaid |
|---|---|
| CHIP Medicaid | Medicare |
| Other public insurance (not CHIP) | Other Public Insurance (CHIP) |
| Private Insurance | |

FIG. 7A

13. During the past year, what was the total combined income for you and the family members you live with? This information will help us determine if you are eligible for any benefits.

_____

| I choose not to answer this question |
|---|

14. In the past year, have you or any family members you live with been unable to get any of the following when it was really needed? Check all that apply.

| Yes | No | Food | Yes | No | Clothing |
|---|---|---|---|---|---|
| Yes | No | Utilities | Yes | No | Child Care |
| Yes | No | Medicine or Any Health Care (Medical, Dental, Mental Health, Vision) | | | |
| Yes | No | Phone | Yes | No | Other (please write): |
| | | I choose not to answer this question | | | |

15. Has lack of transportation kept you from medical appointments, meetings, work, or from getting things needed for daily living? Check all that apply.

| Yes, it has kept me from medical appointments or from getting my medications |
|---|
| Yes, it has kept me from non-medical meetings, appointments, work, or from getting things that I need |
| No |
| I choose not to answer this question |

Social and Emotional Health

16. How often do you see or talk to people that that you care about and feel close to? (For example: talking to friends on the phone, visiting friends or family, going to church or club meetings)

| Less than once a week | 1 or 2 times a week |
|---|---|
| 3 to 5 times a week | 5 or more times a week |
| I choose not to answer this question | |

17. Stress is when someone feels tense, nervous, anxious, or can't sleep at night because their mind is troubled. How stressed are you?

| Not at all | A little bit |
|---|---|
| Somewhat | Quite a bit |
| Very much | I choose not to answer this question |

Optional Additional Questions

18. In the past year, have you spent more than 2 nights in a row in a jail, prison, detention center, or juvenile correctional facility?

| Yes | No | I choose not to answer this question |
|---|---|---|

19. Are you a refugee?

| Yes | No | I choose not to answer this question |
|---|---|---|

20. Do you feel physically and emotionally safe where you currently live?

| Yes | No | Unsure |
|---|---|---|
| I choose not to answer this question | | |

21. In the past year, have you been afraid of your partner or ex-partner?

| Yes | No | Unsure |
|---|---|---|
| I have not had a partner in the past year | | |
| I choose not to answer this question | | |

PROGRAMMATICALLY MANAGING SOCIAL DETERMINANTS OF HEALTH TO PROVIDE ELECTRONIC DATA LINKS WITH THIRD PARTY HEALTH RESOURCES

CROSS-REFERENCE TO RELATED APPLICATIONS

This patent application claims priority from U.S. Provisional Appl. Ser. No. 62/805,500, filed Feb. 14, 2019, which is incorporated herein by reference in its entirety.

BACKGROUND

The medical and healthcare industry has generally focused on providing clinical care to help patients recover from and/or cope with various ailments, injuries, and/or the like. Although some providers also provide preventative care, the healthcare industry has generally been incapable of addressing an individual patient's social determinants of health—those non-clinical factors that have a direct impact on a patient's ability to maintain his/her own health, whether though preventative care or more traditional care recommendations provided by a care provider. Specifically, the healthcare industry has been plagued by technological barriers that prevent the collection of information indicative of social determinants of health, the dissemination of such information to individuals able to utilize such information, and to identify appropriate care structures for patients that address and/or resolve various social determinants of health.

Through applied effort and ingenuity, various limitations existing within the art have been addressed by certain embodiments as discussed herein.

BRIEF SUMMARY

Various embodiments are directed to systems and methods for facilitating utilization of various external resources (e.g., scheduling resources, transportation arrangement resources, and/or the like) and for ascribing data indicative of a provided value to patients to address and/or resolve identified social determinants of health (SDOH) relevant for a particular patient. Such embodiments comprise configurations to receive data (e.g., user input data) from one or more distributed systems indicative of patient-specified SDOH factors and to standardize data indicative of such SDOH factors for inclusion within a patient profile. The standardized SDOH factors may be further utilized to recommend various services for the patient to address and/or resolve the SDOH factors so as to facilitate care for the patient's health. The system may automatically provide various patient data to external systems to facilitate providing the recommended services for the patient, such as data necessary to ensure qualification for the recommended services.

Various embodiments are directed to a computer-implemented method for facilitating access to services based on social determinants of health (SDOH). In certain embodiments, the method comprises: receiving, via a secure data repository, input indicative of SDOH factors for a patient; generating SDOH factor data indicative of the SDOH factors; receiving, via the secure data repository, patient data from a patient profile corresponding to a patient; mapping the SDOH factor data to one or more codes identified within a stored code-base repository via the secure data repository; providing at least a portion of the patient data and the one or more codes to an SDOH repository isolated from the secure data repository; based at least in part on the one or more codes and at least a portion of the patient data retrieved from the patient profile, identifying one or more recommended external service provider computing systems facilitating services for accommodating one or more of the SDOH factors via the SDOH repository; providing, from the SDOH repository, at least a portion of the patient data retrieved from the patient profile to one or more of the recommended external service provider computing systems; querying, via the SDOH repository, a hierarchical data storage repository comprising characteristic data corresponding to each of the plurality of recommended services, wherein the characteristic data is determined based at least in part on supporting resources linked with the hierarchical data storage repository; populating, in association with the SDOH repository, a patient profile corresponding to the patient with the one or more codes and at least a portion of the characteristic data; and generating, in association with the SDOH repository, a visual patient profile dashboard comprising at least a portion of the patient profile.

In various embodiments, providing at least a portion of the patient data retrieved from the patient profile to the one or more external resources comprises: detecting a trigger event indicative of a need for services provided by the one or more external resources; and upon detecting the trigger event, providing the at least a portion of the patient data retrieved from the patient profile to the one or more external resources to initiate the recommended services. In certain embodiments, the method further comprises monitoring usage of the recommended services based at least in part on a monitored frequency of occurrence of detected trigger events. Moreover, in certain embodiments, the method further comprises populating the patient profile with usage data indicative of usage of the recommended services. In various embodiments, the usage data comprises an annualized cost determined based at least in part on a monitored usage of the recommended services and characteristic data corresponding to the recommended services. In certain embodiments, the method further comprises prior to providing at least a portion of the patient data and the one or more codes to the SDOH repository, anonymizing, at the secure data repository, at least a portion of the patient data comprising the one or more codes; consolidating anonymized patient data for a plurality of patients via the SDOH repository; and generating one or more SDOH reports comprising the anonymized patient data for the plurality of patients. In certain embodiments, the hierarchical data storage repository comprises a first data storage level identifying a plurality of service types and a second storage level within each first data storage level, wherein the second storage level identifies a plurality of services, wherein each of the plurality of services has associated characteristic data.

Certain embodiments are directed to a system for facilitating access to services based on social determinants of health (SDOH), the system comprising: one or more memory storage repositories comprising a secure data storage repository and an SDOH repository; one or more processors configured to independently access data within one of the secure data storage repository and the SDOH repository, wherein the one or more processors are collectively configured to: receive input indicative of SDOH factors for a patient; store the input indicative of the SDOH factors the patient within the secure data repository; generate SDOH factor data indicative of the SDOH factors in association with the secure data repository; receive, via the secure data repository, patient data from a patient profile corresponding to a patient; map the SDOH factor data to one or more codes identified within a stored code-base repository in association with the secure data repository; providing at least a portion of the patient data and the one or more codes to the SDOH repository; based at least in part on the one or more codes and at least a portion of the patient data retrieved from the patient profile, identify one or more recommended external service provider computing systems facilitating services for accommodating one or more of the SDOH factors via the SDOH repository; provide, from the SDOH repository, at least a portion of the patient data retrieved from the patient profile to one or more of the recommended external service provider computing systems; query, via the SDOH repository, a hierarchical data storage repository comprising characteristic data corresponding to each of the plurality of recommended services, wherein the characteristic data is determined based at least in part on supporting resources linked with the hierarchical data storage repository; populate, in association with the SDOH repository, a patient profile corresponding to the patient with the one or more codes and at least a portion of the characteristic data; and generate, in association with the SDOH repository, a visual patient profile dashboard comprising at least a portion of the patient profile.

In various embodiments, providing at least a portion of the patient data retrieved from the patient profile to the one or more external resources comprises: detecting a trigger event indicative of a need for services provided by the one or more external resources; and upon detecting the trigger event, providing the at least a portion of the patient data retrieved from the patient profile to the one or more external resources to initiate the recommended services. Moreover, in certain embodiments, the one or more processors are further configured to: monitor usage of the recommended services based at least in part on a monitored frequency of occurrence of detected trigger events. In certain embodiments, the one or more processors are further configured to populate the patient profile with usage data indicative of usage of the recommended services. In various embodiments, the usage data comprises an annualized cost determined based at least in part on a monitored usage of the recommended services and characteristic data corresponding to the recommended services. In certain embodiments, the one or more processors are further configured to: prior to providing at least a portion of the patient data and the one or more codes to the SDOH repository, anonymize, at the secure data repository, at least a portion of the patient data comprising the one or more codes; consolidate anonymized patient data for a plurality of patients via the SDOH repository; and generate one or more SDOH reports comprising the anonymized patient data for the plurality of patients.

In various embodiments, the hierarchical data storage repository comprises a first data storage level identifying a plurality of service types and a second storage level within each first data storage level, wherein the second storage level identifies a plurality of services, wherein each of the plurality of services has associated characteristic data.

Certain embodiments are directed to a computer program product comprising a non-transitory computer readable medium having computer program instructions stored therein, the computer program instructions when executed by a processor, cause the processor to: receive input indicative of social determinants of health (SDOH) factors for a patient; store the input indicative of the SDOH factors within a secure data repository; generate SDOH factor data indicative of the SDOH factors in association with the secure data repository; receive, via the secure data repository, patient data from a patient profile corresponding to a patient; map the SDOH factor data to one or more codes identified within a stored code-base repository in association with the secure data repository; providing at least a portion of the patient data and the one or more codes to a SDOH repository; based at least in part on the one or more codes and at least a portion of the patient data retrieved from the patient profile, identify one or more recommended external service provider computing systems facilitating services for accommodating one or more of the SDOH factors via the SDOH repository; provide, from the SDOH repository, at least a portion of the patient data retrieved from the patient profile to one or more of the recommended external service provider computing systems; query, via the SDOH repository, a hierarchical data storage repository comprising characteristic data corresponding to each of the plurality of recommended services, wherein the characteristic data is determined based at least in part on supporting resources linked with the hierarchical data storage repository; populate, in association with the SDOH repository, a patient profile corresponding to the patient with the one or more codes and at least a portion of the characteristic data; and generate, in association with the SDOH repository, a visual patient profile dashboard comprising at least a portion of the patient profile.

In certain embodiments, providing at least a portion of the patient data retrieved from the patient profile to the one or more external resources comprises: detecting a trigger event indicative of a need for services provided by the one or more external resources; and upon detecting the trigger event, providing the at least a portion of the patient data retrieved from the patient profile to the one or more external resources to initiate the recommended services. In various embodiments, the computer program instructions when executed by a processor, cause the processor to further: monitor usage of the recommended services based at least in part on a monitored frequency of occurrence of detected trigger events. In certain embodiments, the usage data comprises an annualized cost determined based at least in part on a monitored usage of the recommended services and characteristic data corresponding to the recommended services. Moreover, in various embodiments, the computer program instructions when executed by a processor, cause the processor to further: prior to providing at least a portion of the patient data and the one or more codes to the SDOH repository, anonymize, at the secure data repository, at least a portion of the patient data comprising the one or more codes; consolidate anonymized patient data for a plurality of patients via the SDOH repository; and generate one or more SDOH reports comprising the anonymized patient data for the plurality of patients. In various embodiments, the hierarchical data storage repository comprises a first data storage level identifying a plurality of service types and a second storage level within each first data storage level, wherein the second storage level identifies a plurality of services, wherein each of the plurality of services has associated characteristic data.

BRIEF DESCRIPTION OF THE SEVERAL VIEWS OF THE DRAWINGS

Reference will now be made to the accompanying drawings, which are not necessarily drawn to scale, and wherein:

FIGS. 7A-7B illustrate example forms for receiving user input indicative of self-reported social determinants of health in accordance with certain embodiments.

DETAILED DESCRIPTION

Figure 1:
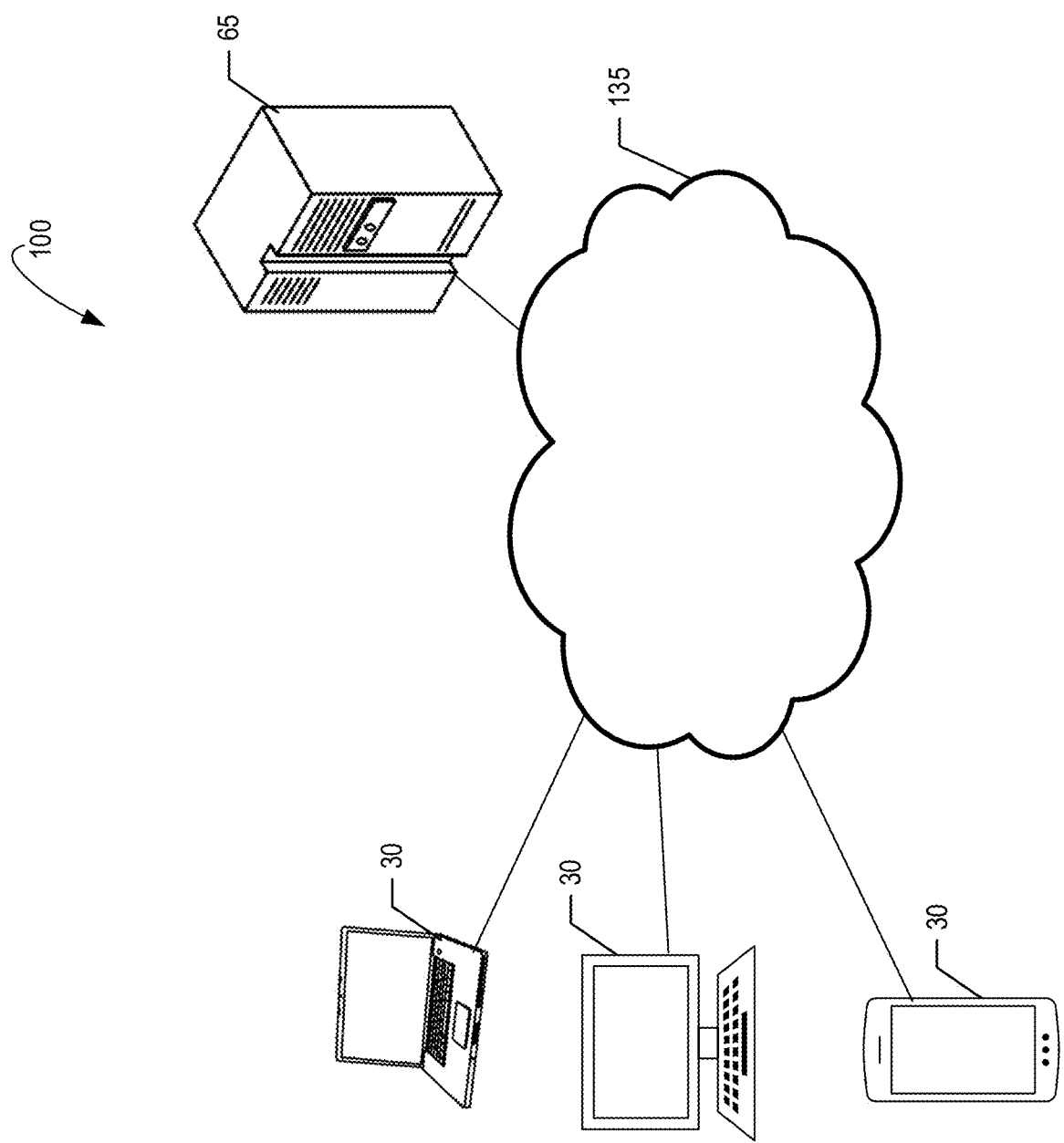
FIG. 1 is a diagram of a system that can be used in conjunction with various embodiments of the present invention.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

I. Computer Program Products, Methods, and Computing Entities

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. Exemplary System Architecture

FIG. 1 provides an illustration of a system 100 that can be used in conjunction with various embodiments of the present invention. As shown in FIG. 1, the system 100 may comprise one or more analytic computing entities 65, one or more user computing entities 30, one or more networks 135, and/or the like. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, standalone entities, the various embodiments are not limited to this particular architecture.

a. Exemplary Analytic Computing Entity

Figure 2A:
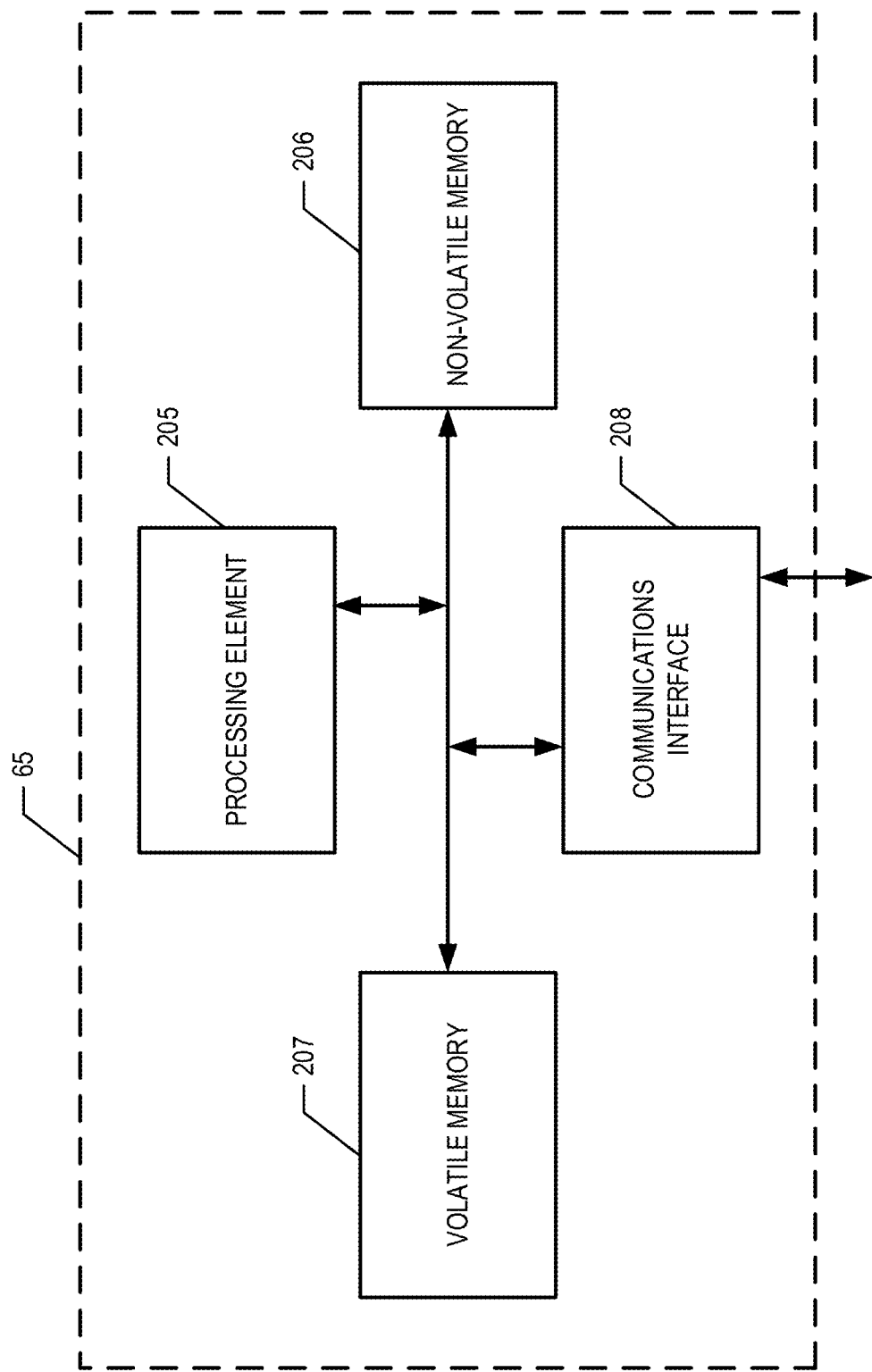
FIG. 2A is a schematic of an analytic computing entity in accordance with certain embodiments of the present invention.

FIG. 2A provides a schematic of an analytic computing entity 65 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the analytic computing entity 65 may communicate with other computing entities, one or more user computing entities 30, and/or the like.

As shown in FIG. 2A, in one embodiment, the analytic computing entity 65 may include or be in communication with one or more processing elements 205 (also referred to as processors, processing circuitry, and/or similar terms used herein interchangeably) that communicate with other elements within the analytic computing entity 65 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the analytic computing entity 65 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, metadata repositories database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Memory media 206 (e.g., metadata repository) may also be embodied as a data storage device or devices, as a separate database server or servers, or as a combination of data storage devices and separate database servers. Further, in some embodiments, memory media 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third party provider and where some or all of the information/data required for the operation of the system may be stored. As a person of ordinary skill in the art would recognize, the information/data required for the operation of the system may also be partially stored in the cloud data storage system and partially stored in a locally maintained data storage system.

Figure 2B:
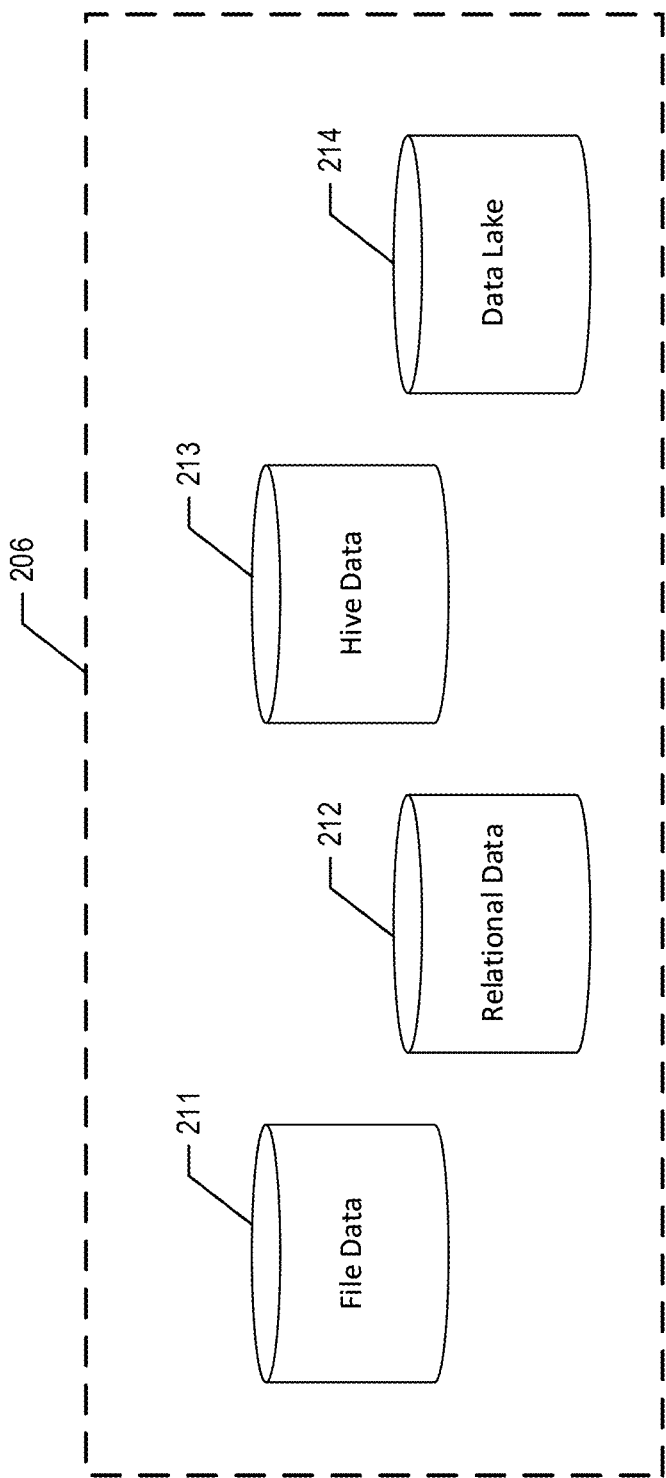
FIG. 2B is a schematic representation of a memory media storing a plurality of data assets.

Memory media 206 (e.g., metadata repository) may include information/data accessed and stored by the system to facilitate the operations of the system. More specifically, memory media 206 may encompass one or more data stores configured to store information/data usable in certain embodiments. For example, as shown in FIG. 2B, metadata for data assets may be stored in metadata repositories encompassed within the memory media 206. The metadata for the data assets in the metadata data stores, metadata repositories, and similar words used herein interchangeably may comprise file information/data 211, relational information/data 212, Hive information/data 213, data lake information information/data 214, and/or various other types of information/data. Data stored within such data repositories may be utilized during operation of various embodiments as discussed herein. Moreover, it should be understood that individual data repositories may be further subdivided into a plurality of separately accessible data storage areas that are sufficiently isolated from one another so as to prevent undesired data transfers between such data storage repositories. For example and as discussed in greater detail herein, the mentioned data lake 214 may be further subdivided into at least a secure data repository operating as a secure lockbox of data/information, that thereby protected data stored therein (e.g., sensitive patient data) and a SDOH repository accessible via a plurality of external data resources so as to facilitate patient access to various services provided at least in part via those external data resources. As will be recognized, metadata repositories are inventories data assets in an organization's environment.

In one embodiment, the analytic computing entity 65 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the analytic computing entity 65 with the assistance of the processing element 205 and operating system.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the analytic computing entity 65 may communicate with computing entities or communication interfaces of other computing entities, user computing entities 30, and/or the like. In this regard, the analytic computing entity 65 may access various data assets.

As indicated, in one embodiment, the analytic computing entity 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the analytic computing entity 65 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The analytic computing entity 65 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the analytic computing entity's components may be located remotely from other analytic computing entity 65 components, such as in a distributed system. Furthermore, one or more of the components may be aggregated and additional components performing functions described herein may be included in the analytic computing entity 65. Thus, the analytic computing entity 65 can be adapted to accommodate a variety of needs and circumstances.

b. Exemplary User Computing Entity

Figure 3:
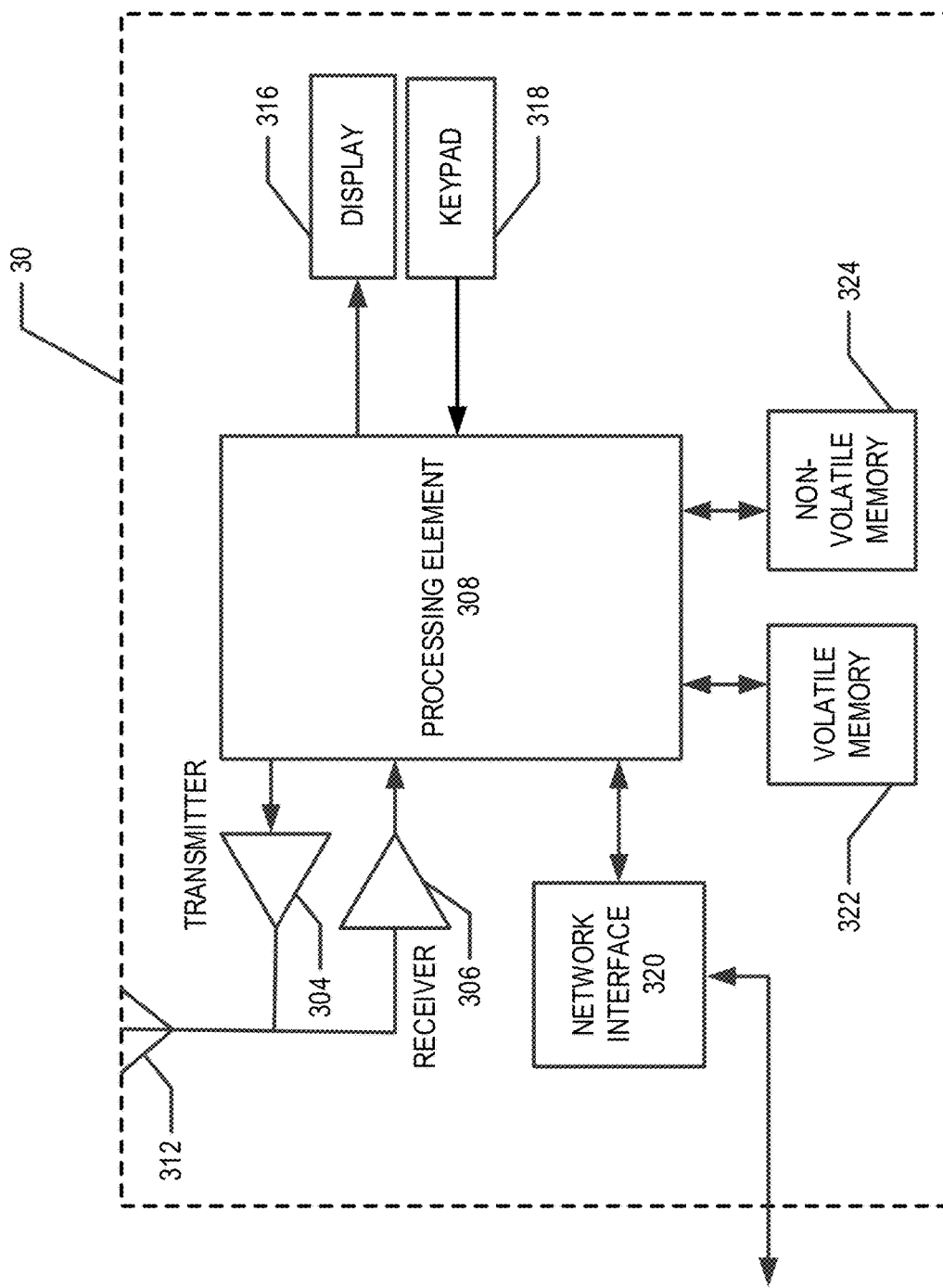
FIG. 3 is a schematic of a user computing entity in accordance with certain embodiments of the present invention.

FIG. 3 provides an illustrative schematic representative of user computing entity 30 that can be used in conjunction with embodiments of the present invention. As will be recognized, the user computing entity may be operated by an agent and include components and features similar to those described in conjunction with the analytic computing entity 65. Further, as shown in FIG. 3, the user computing entity may include additional components and features. For example, the user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as an analytic computing entity 65, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing entity 30 may operate in accordance with multiple wireless communication standards and protocols, such as GPRS, UMTS, CDMA2000, 1xRTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise a user interface 1100 comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 30 to cause display or audible presentation of information/data and for user interaction therewith via one or more user input interfaces. The user output interface may be updated dynamically from communication with the analytic computing entity 65. The user input interface can comprise any of a number of devices allowing the user computing entity 30 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Exemplary Networks

In one embodiment, the networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

III. Exemplary System Operation

Details regarding various embodiments are described with respect to FIGS. 4-12 herein. As discussed in detail, configurations for addressing patient-specific SDOH barriers to care through the identification and classification of such SDOH barriers to care and for generating referral data for patients to obtain applicable services to address and/or resolve those SDOH barriers to care may be provided to increase the overall healthcare satisfaction of patients. Such configurations may additionally address other goals of the healthcare industry, such as reducing unnecessary utilization of healthcare services (e.g., reducing the quantity of non-acute emergency department visits by various patients, reducing avoidable readmission rates for patients, and/or the like), trading high-cost services for low-cost care options (e.g., expanding primary care access as to avoid more costly emergency department visits by patients, expanding availability of medical home enrollment for patients with limited mobility and/or transportation options so as to avoid costly ambulance transportation and associated costly emergency department visits), and enhancing patient engagement and care coordination (e.g., for chronic condition management, for improved referrals to specialists when necessary, and/or the like). To ascertain various mechanisms by which these and other goals of healthcare can be achieved, certain embodiments incorporate analysis of various non-clinical factors that may impact a patient's health, such as whether the patient has stable housing, whether the patient has access to healthy food options, whether the patient has educational opportunities, whether the patient has access to transportation, whether the patient has access to parks, playgrounds, and other facilities promoting a general healthy lifestyle, among other non-clinical factors that may contribute to a patient's overall health and wellbeing.

In certain embodiments, these configurations may be implemented together with certain configurations for ascribing data indicative of various characteristics to patient profiles based at least in part on services provided/referred to the patient. Such characteristic data may be retrieved from one or more sources having a corresponding confidence level attributed to characteristic data provided by each of the one or more sources. As just one example, the characteristic data may identify a value provided to the patient via the referral/service, which may vary based at least in part on a frequency with which the patient utilizes the referral/service. Moreover, certain embodiments may monitor usage of various services (e.g., based at least in part on usage data generated and/or provided by computing entities associated with the service provider), so as to provide accurate determinations of value provided to the patient.

a. Overview

Various embodiments facilitate access to one or more services (e.g., services provided by one or more entities each having discrete computing environments in communication via a network (e.g., the internet) with an analytic computing entity) to aid patients based at least in part on identified SDOH factors applicable to the patients. Data indicative of one or more patient-specific SDOH factors is received at an analytic computing entity, for example, from distributed computing entities (e.g., user computing entities associated with healthcare providers, patients, and/or the like). This SDOH factor data is standardized and provided in a flattened data file that may be integrated and/or linked with existing patient data. In certain embodiments, standardization of the SDOH factor data comprises mapping the SDOH factor data with one or more SDOH-relevant codes, such as ICD-10 codes, Z-codes, and/or the like that may be utilized across healthcare-related computing systems, and which may be utilized as compressed indications of the those SDOH factors relevant to each specific patient.

Based on the determined SDOH-specific codes for each specific patient (and in certain embodiments based partially on additional patient data (e.g., medical data), the analytic computing entity identifies one or more recommended services for the patient to address and/or resolve the SDOH factors of the patient. Those recommended services may be initiated/provided at least partially via one or more external computing systems (e.g., computing systems associated with third-party service providers). Thus, the analytic computing entity may be configured to transmit at least a portion of patient data to applicable external computing systems to initiate the one or more recommended services. Moreover, the recommended services may be associated with characteristic data stored within and/or otherwise accessible to the analytic computing entity. The characteristic data is indicative of various characteristics of these services, such as data indicative of a value that such services provide to a patient, data indicative of how often such services may be utilized, data indicative of various SDOH factors that may be addressed and/or resolved with such services, and/or the like.

Moreover, the analytic computing entity may be configured to monitor usage of the one or more recommended services, for example, based at least in part on identified transfers of data to the external systems. The analytic computing entity may be further configured to identify one or more resources indicative of characteristics of those recommended services (e.g., the resources being stored and/or linked from one or more hierarchical data storage repositories storing data indicative of characteristics of various services), so as to determine an estimated value to the patient of utilizing the services. In various embodiments, the analytic computing entity may be further configured to utilize additional resources to identify an estimated cost savings associated with providing access to the recommended services as compared with predicted detrimental health outcomes for the patient if those services were not provided, based at least in part on the SDOH factors attributable to the patient.

1. Technical Problem

Historically, healthcare providers often had little insight into SDOH factors of their patients (e.g., inaccessibility to healthy food, inaccessibility to transportation, inability to pay for necessary medications, utilities, or other basic necessities), and therefore those healthcare providers were limited in their ability to provide appropriate care services to patients to address and/or resolve SDOH factors. For example, healthcare providers needed to expend significant time and energy (beyond what is typically required in providing care) to learn about SDOH factors impacting each individual patient separately, and then to make judgement decisions on how best to address and/or resolve those SDOH factors in care decisions (and/or to determine whether those SDOH factors should be considered in care decisions at all). However, existing systems had limited insight into SDOH factors of individual patients, some care decisions may be unavailable based on existing payment infrastructures, or those care decisions may be deemed incorrect based on currently known and/or understood healthcare science. Alternatively, care providers can provide care and/or care recommendations without regard to SDOH factors that may impact a patient, thereby leaving the patient vulnerable to potential gaps in care if the patient is incapable of adhering to the care recommendations provided by the care provider.

Moreover, because identified services, referrals, and/or other processes for addressing SDOH factors of patients are generally difficult to track, there has historically been no mechanism by which the total value received by a patient could be determined when utilizing services for addressing SDOH factors. Accordingly, cost-based monitoring services were previously incapable of tracking value received by the patient, for example, which may be utilized for determining the applicability of other potential services that may be offered to the patient.

2. Technical Solution

To address the above-mentioned technical problems, various embodiments provide a standardized coding for SDOH factors of patients to be recognized by various healthcare-related computing systems (e.g., the analytic computing entity, user computing entities executing one or more healthcare software systems, such as electronic medical record (EMR) related systems, scheduling systems, and/or the like), external computing entities associated with various service providers, and/or the like.

Moreover, an analytic computing entity configured in accordance with various embodiments integrates SDOH related factors for specific patients into patient-specific profiles having additional patient data stored therein. Together with at least a portion of the additional patient data, such as medical-related data, the analytic computing entity 65 may identify recommended services to address and/or resolve the SDOH factors specific to the patient. In instances in which those recommended services are utilized by the patient (e.g., under the supervision of a healthcare provider and/or by the patient alone), the analytic computing entity may facilitate usage of those services, for example, by initiating the services through the transmission of relevant patient data to one or more service provider operated computing systems. As just one example, upon determining that a patient has limited access to transportation to reach medically necessary dialysis treatment appointments, the analytic computing entity may automatically provide patient-specific data to one or more transportation-providing service providers (and their computing entities), to enable the transportation-providing service providers determine the patient's qualifications for receiving transportation services, and for identifying relevant patient-specific location data to enable a vehicle to reach the patient to transport the patient to a dialysis center.

The analytic computing entity may be further configured to track the usage of various recommended services, and to determine a financial impact of the usage of those recommended services on the patient and/or a payer. For example, by tracking the usage of the recommended services, the analytic computing entity may determine an estimated financial benefit received by the patient through the usage of the referred services. In certain embodiments, the analytic computing entity may be configured to determine an estimated cost to the payer if the services were not provided (e.g., based on estimated care costs to address detrimental healthcare outcomes for the patient if the SDOH factors were not addressed in light of existing medical data) or otherwise for generating data representative of an estimated payment (e.g., data to be used as a proxy for payment), thereby enabling an identification of net estimated financial benefits to the payer by providing access to the recommended services to address and/or resolve known SDOH associated with the patient.

b. Social Determinants of Health

Social Determinants of Health (SDOH) are non-clinical characteristics of a patient that influence the patient's overall health. These SDOH factors inform the conditions in which people live, work, play, learn, worship, and age that shape the conditions of daily life and contribute to a person's health status. SDOH factors comprise, for example, factors such as income, literacy, access to health services, access to educational services, social support, exposure to crime and violence, and the social and physical environment in which a particular individual lives. SDOH factors may, for certain individuals create barriers to care for those individuals, such as SDOH factors that create financial burdens for the individual to access the high cost of care, safe housing, food security, and/or access to social services and/or supports. Particularly for chronically ill patients, the barriers that arise for some patients may drastically impact the patient's overall health and quality of life. SDOH factors may be categorized in various categories, such as SDOH factors reflective of a patient's economic stability (e.g., income level, level of expenses, debt, medical bills, financial support, and/or the like, which may influence the patient's ability to pay for certain medical care), SDOH factors reflective of a patient's neighborhood and physical environment (e.g., housing, access to transportation, safety, and/or the like, which may impact a patient's ability to access medical care), SDOH factors reflective of a patient's access to food, which may directly impact the patient's health and nutrition, SDOH factors indicative of a patient's community and social context (e.g., social integration, available social support systems, community engagement, and/or the like, which may influence the likelihood that a patient will reach out for medical help when needed), SDOH factors indicative of available healthcare services for the patient (e.g., health coverage, provider availability, provider linguistic and cultural competency, quality of care, and/or the like), and/or the like. As discussed herein, such factors could not previously be assigned a value (or any data indicative of a value of services/referrals associated with assisting individuals with addressing SDOH factors) through systematic diagnosis and/or providing a value to intervention services provided.

Assessing SDOH factors for individuals can be critical to understanding an individual's needs and characteristics. In many cases, these SDOH factors may significantly negatively impact an individual's quality of life and health outcomes and addressing SDOH barriers to care may make significant increases in the quality of life and health of an individual. Indeed, certain studies have found that traditional clinical care may be a minor overall contributing factor to the health of a particular individual, with factors such as the individual's health behaviors, social and economic factors of the individual, and physical environment in which the individual lives collectively having a much greater overall contribution on the health of the individual.

As just one example demonstrating the importance of a full understanding of SDOH factors for a particular individual, imagine a hypothetical individual named Janet. Janet is 84 years old, lives alone, has an income at or below the federal poverty line, takes prescription medications, and has no access to transportation. After learning that Janet has not been filling her prescriptions, clinical staff calls Janet to understand why she hasn't picked up her prescription. Janet informs the clinical staff that she understands that she needs to refrigerate her medicine, but she is worried about paying her electric bill. She is concerned that she may not have a way to keep her medicine cold, and so she decides not to pick up her prescription. However, because Janet does not pick up-or take-her prescriptions, her health deteriorates and she enters a repeating cycle of hospitalization that could be avoided if she regularly took her medication. Understanding the SDOH factors of Janet, it can be determined that Janet's circumstances could be drastically improved with a referral to an appropriate service providing assistance to pay her utility bills and/or to provide transportation to pick up her medication. When services/referrals are provided (e.g., to external systems) the analytic computing entity may be configured to generate data indicative of a value of the provided services/referrals such that these services/referrals may be evaluated and/or measured (e.g., together with clinical interventions). This value may be systematically assigned, for example, to support industry-wide development of appropriate benefit plans.

Based on various studies, it has been found that many individuals face barriers in paying for prescriptions, paying for utilities, dealing with stress, paying for medical care, having adequate social interactions, having access to adequate food and safe drinking water, and having access to transportation, as just a few examples. Knowledge of these SDOH factors allows for tailoring of care plans due to those SDOH factors that will improve overall health outcomes. Moreover, specific SDOH factors may become critical in certain settings. The more specific knowledge of SDOH factors attributable to a particular individual, the more targeted the adjustment of an individual's care plan can become. For example, upon identifying housing insecurity and/or social isolation as a major SDOH factor attributable to a particular individual, a care provider may adjust the individual's discharge plans from an acute care setting. Moreover, economic factors (such as inability to afford a drug or copay) may play a role in an individual's adherence to a medication regimen. Food insecurity may play a critical role in treatment of diabetic individuals. Transportation needs may be critical for individuals with treatment plans that require frequent face-to-face contact, dialysis, cancer treatment, rehabilitation services, and/or the like. Illiteracy may drive a care plan/treatment method communication mode and health literacy is a large part of a transplant success, as it requires adherence with complex medication schedules, dietary recommendations, management of co-morbid conditions, and/or the like.

While some care providers today obtain information about various SDOH factors attributable to various individuals, this information is not widely shared with other care providers who interact with the patient, as there is no existing easily usable mechanisms for disseminating such information. For example, facility discharge summaries identify problematic attributes associated with discharge-related attributes of a patient, specialists may not obtain information about various problems that the patient informs them of, health plans may list chronic conditions, and/or the like. However, these sources of information may not be easily communicated to other care providers in an easily accessible manner. Accordingly, various care providers may operate without complete and accurate information regarding SDOH factors of particular individuals when providing care.

Providing services to individuals with unique and/or difficult SDOH factors remains a nascent industry at present, however there are certain government and private services already in existence that are designed to help individuals in addressing certain barriers to healthcare. However, these programs are not always well-known to those individuals who need them, and in fact many individuals who qualify may be unaware of their eligibility for these programs. For example, government subsidy programs for Medicare Secondary Payer coverage is available for certain individuals, government subsidy programs such as Low-Income Subsidy programs are available for certain low-income individuals, and recertification support for Medicaid programs are available for various individuals. Private and social programs, such as social service referral programs for certain healthcare plan members are available, Veteran identification and care coordination programs are available for military veterans, alternative ride programs are available for certain qualifying individuals, commercial social service reporting frameworks are available for maintaining information about the healthcare of individuals enrolled in certain health plans, and many other programs are provided through private and public entities. Many individuals may be entirely unaware of these programs' existence and/or their eligibility for use.

c. Medical Data Storage Environment

Figure 4A:
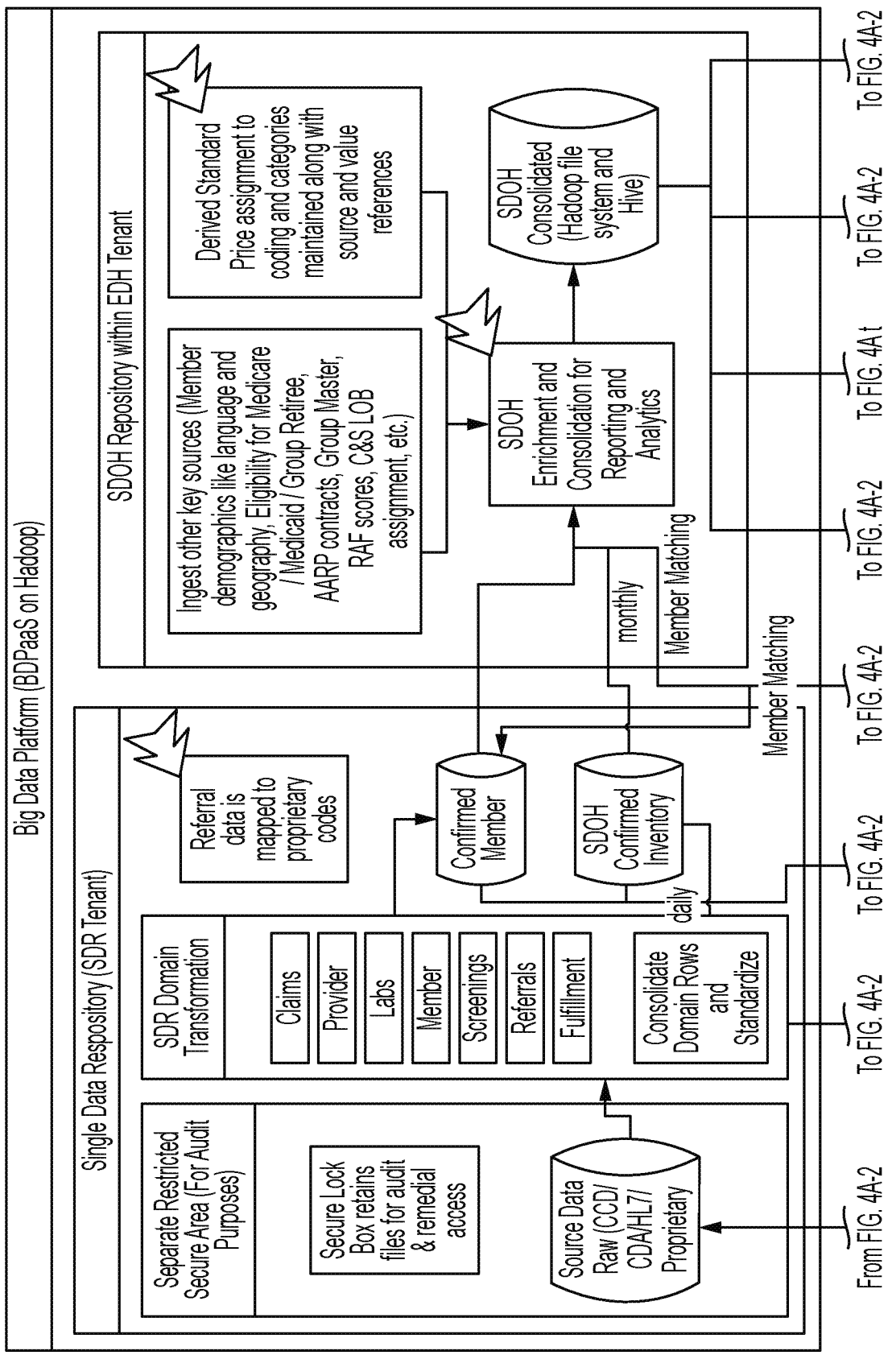
FIGS. 4A-4C schematically illustrate various functions of system components in accordance with certain embodiments.
Figures 2, 4A:
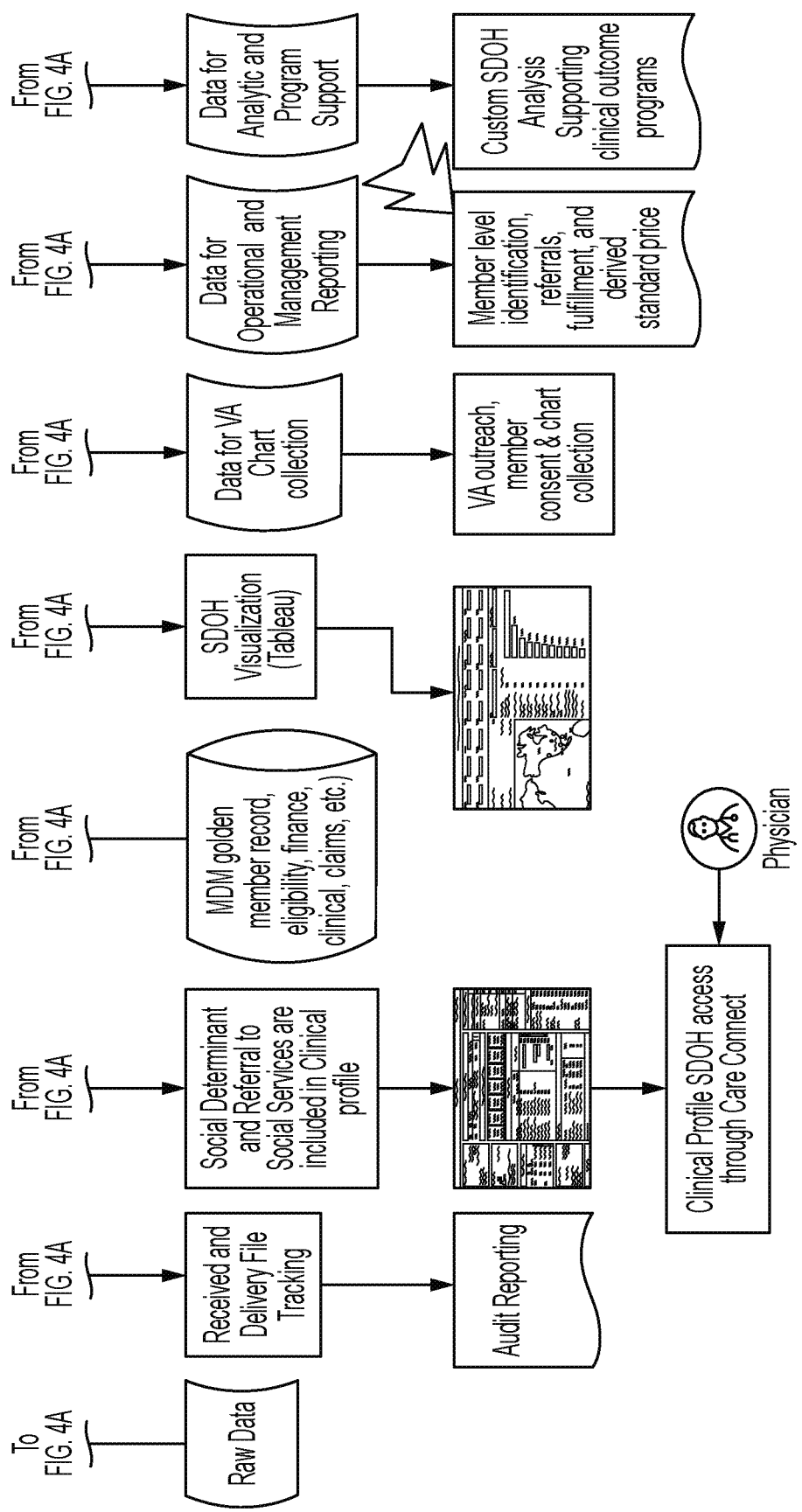
Figure 4B:
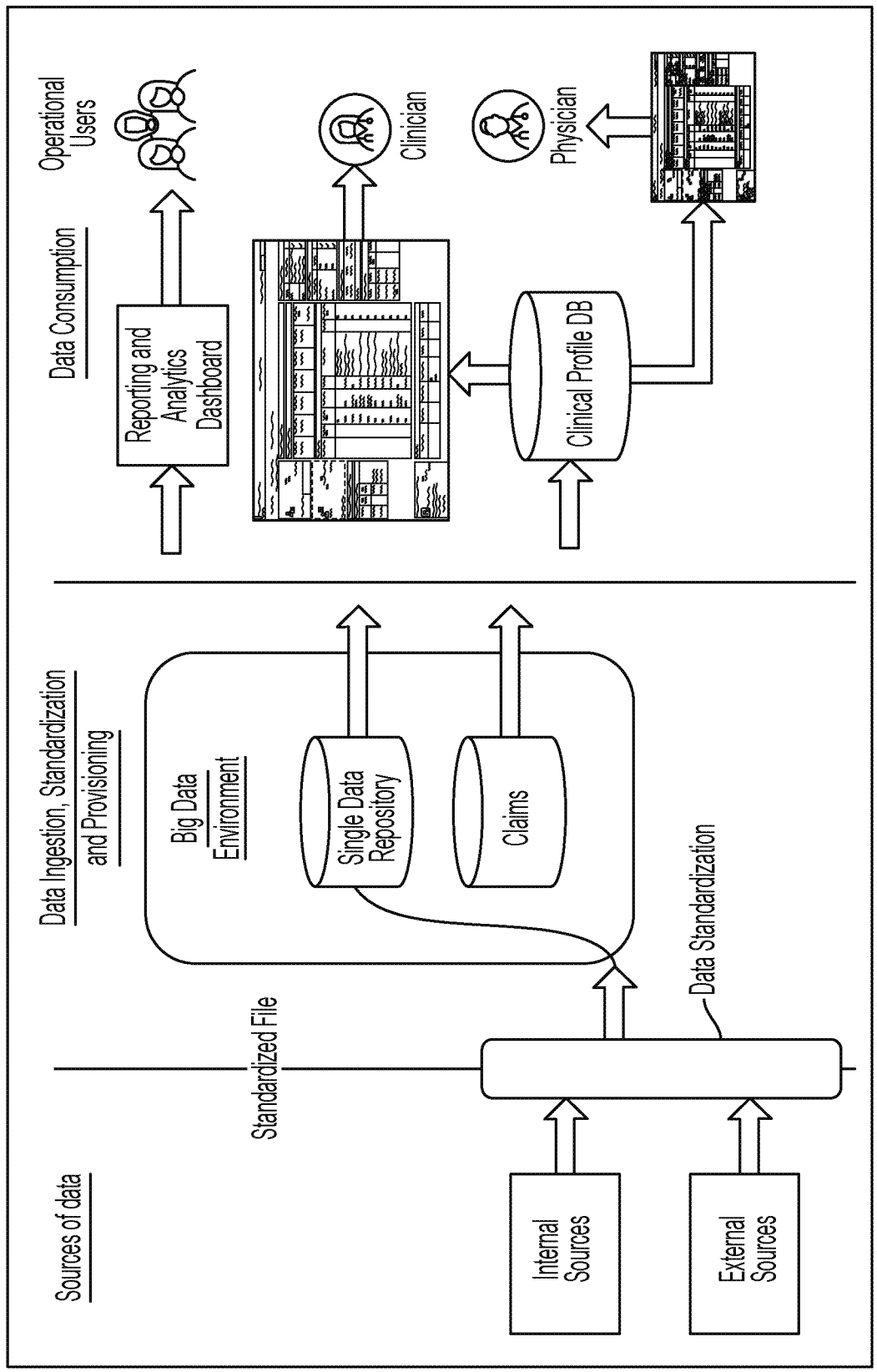
Figure 4C:
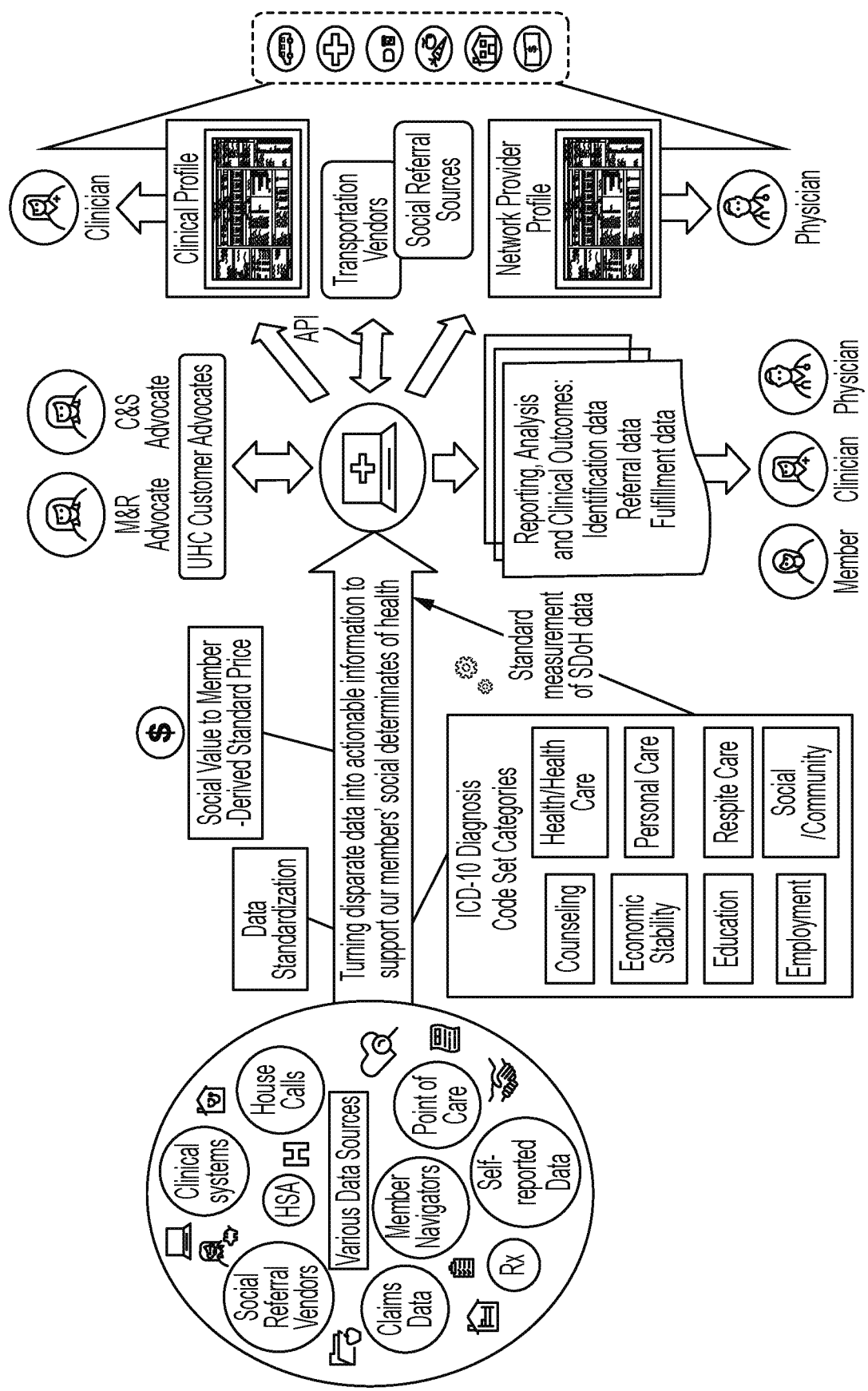

FIGS. 4A-4C encompass illustrations of various components and their functionalities within a medical data storage environment in which patient data indicative of various SDOH factors attributable to an individual may be provided and stored within an environment as illustrated in FIGS. 4A-4C, which may facilitate various configurations as discussed in greater detail herein. Various embodiments are implemented as scalable clusters of processing and/or storage resources. In certain embodiments, the processing and storage resources may be assigned for various tasks, for example, via assigned individual and/or system identifiers utilized to support the various computing and storage resources.

As illustrated, a data storage environment may be embodied as a "big data" environment configured for obtaining and/or storing data received from a plurality of data sources and performing various big data analysis procedures to generate outputs for differing anticipated uses. For example, data may be input from internal data sources (e.g., accessible directly by an analytic computing entity 65) and/or external data sources (e.g., accessible via a network by the analytic computing entity 65 and operated by one or more third parties as compared with the analytic computing entity 65). The received data may be standardized into a standardized file format as discussed herein to facilitate ingestion, storage, management, and/or usage by the analytic computing entity 65 within the big data environment. Moreover, the standardized data file may be generated within a secure data storage environment (e.g., inaccessible for read access by external computing entities) and provided to an externally accessible data storage repository to facilitate providing access to various services provided by the one or more external resources to a patient. As discussed in greater detail herein, such data may comprise data indicative of various patient-specific data that may be utilized to identify applicable barriers to care, and/or data indicative of various services that may be utilized for addressing corresponding barriers to care. The data may be received as input to a single data repository as illustrated in FIGS. 4A-4C for analysis along with specific claims data, for example, corresponding to particular healthcare claims generated in association with particular patients. Through various analysis and data generation configurations as discussed herein, the analytic computing entity 65 generates data outputs for one or more reporting and/or analytics dashboards (e.g., generated for and accessible by patients), healthcare profile dashboards (e.g., generated for and accessible by healthcare providers treating a corresponding patient), and/or for providing data into a clinical care profile database, for example, for attribution to patient profiles that may be utilized to populate various analytic and/or reporting systems, profiles, dashboards, reports, and/or the like, for example, by external systems configured to consume data within a patient profile and, for example, for initializing access to one or more services provided at least in part via the external systems.

Various embodiments may be implemented within a consolidated data storage platform (e.g., a "big data" storage platform) that may operate via any of a variety of data storage environmental structures, such as Hadoop structures in certain embodiments. Moreover, data may be ingested into the data storage environment via an intake module, which may be implemented as a discrete repository tenant, such as a Single Data Repository (SDR Tenant). The SDR Tenant may accompany an SDOH Repository, wherein the SDOH Repository contains additional data specific to particular patients (e.g., patient medical data), data utilized for assigning and/or determining various service characteristics (e.g., derived standard pricing data, for example, which may be reflective of market pricing for various services), and/or the like. In certain embodiments, the SDR Tenant may be configured for temporarily storing certain data received from various data sources, such as from various EMR systems operating at physician user computing entities, from patient-operated user computing entities (e.g., providing data directly to the monitoring server, and/or the like), and/or the like before providing applicable data to various reporting configurations and/or for providing data to the SDOH repository for storage and later retrieval. In certain embodiments, the SDR Tenant is isolated from the SDOH repository to enable the SDR Tenant to operate as a secure lockbox for received data (e.g., storing data permanently and/or temporarily for an extended time period). Only specific data (e.g., data that has been scrubbed of certain private patient data) may be provided from the SDR Tenant to the SDOH repository in accordance with certain embodiments. The secure lockbox may encrypt included data such that data may not be accessed except under specified circumstances, such as during an audit process. The secure lockbox may be configured for storing received raw data, for example, prior to data standardization, prior to one or more data filtering processes, and/or the like implemented prior to generation of various reports and/or ingestion of data into the SDOH repository. Moreover, the secure lockbox configuration of the SDR may be utilized for generating appropriate data files comprising data suitable for providing to the SDOH repository (and therefore suitable for providing to various external computing systems). Via one or more interface configurations of the data storage platform, data may be provided to a variety of systems and/or computing entities to execute various processes as discussed herein.

In certain embodiments, non-clinical data identification, referral and fulfillment records are received via the SDR Tenant and stored within the SDOH Repository. Additional patient data may be received directly into the SDOH Repository (e.g., from data sources configured for generating data within an ingestible data storage format for the SDOH repository), such as patient eligibility data for various health plans, business segment data, demographic data, Medicare risk scores (e.g., most-current Medicare risk score), Employer group names for group retirees, line of business data for Medicaid members, and/or the like. This internal data may be joined with externally sourced data (e.g., geographic data) for reporting and/or filtering as discussed herein. Data indicative of derived standard pricing models may be received directly (or indirectly) at the SDOH repository, for populating service characteristic data stored within one or more service profiles at the SDOH repository (e.g., stored within a hierarchical data storage repository for the services supported within the SDOH repository). A detailed discussion regarding configurations for receiving and ingesting service characteristic data including derived standard pricing data is provided below.

Finally, additional data from other external data sources, such as claims data specific to particular patient-specific claims, location data, financial data, program eligibility data, and/or the like may be received at the SDOH repository in certain embodiments for further enriching stored data indicative of particular patients, services, and/or the like.

Data within the SDOH repository is updated periodically, for example, upon a defined schedule. The illustrated example of FIG. 4 shows a monthly update schedule, however it should be understood that other update schedules may be utilized in various embodiments. In certain embodiments, after updating data stored within the SDOH repository, data stored therein (regardless of data source) may be replicated into a Hive data structure within the same SDOH repository environment to enable direct connection for tableau reporting, operational reporting, and other analytical uses of Structured Query Language (SQL) access.

The configuration may be additionally provided for generating outputs that may be ingested by various reporting systems, for directly generating reports, dashboards, and/or the like for various users (e.g., patients, healthcare providers, and/or the like). For example, the SDR Tenant may be configured for providing data indicative of various barriers to care to clinical profiles corresponding to particular patients (e.g., on a regular basis, such as daily), thereby enabling quick review of potential data indicative of barriers to care of a patient by a provider. Other, more detailed data that may be subject to analysis and reporting of the SDOH data may additionally be provided in various output formats. For example, SDOH visualizations (for example, which may include data regarding derived standard pricing, or value received by patients, in the aggregate, as a result of services provided to address various SDOH factors) may be generated as certain reports, which may be anonymized of any patient data and may be provided to illustrate the pervasiveness of certain barriers to care and/or other social determinants of health within a particular population of patients. Other reports may also be generated, for example, based at least in part on patient data, such as data indicative of various veterans reflected within the data, data provided for operational and/or management-related reporting (e.g., indicating patient memberships for those patients referred to one or more services, indicating rates of fulfillment of referred services, indicating derived standard prices for fulfilled services, and/or the like). Other data may also be provided for additional reporting, such as analytic and program support reporting data, which may indicate the effectiveness of various programs and services provided through the referral programs implemented by the analytic computing entity 65.

In certain embodiments the SDR Tenant is configured to receive data from a plurality of data sources and to provide adequate access security and data isolation to avoid providing data to one or more unauthorized data viewers (directly or indirectly) having access to other portions of the data (e.g., to data stored within the SDOH repository). For example, raw data and/or parsed data received from various data sources may include certain data regarding patients for which data viewing and/or analysis access is not permitted. Accordingly, this data may be ingested directly into a secure lockbox and stored therein for audit purposes only. Data within the lockbox configuration may additionally be supplemented by various pseudo claim data that may be utilized to identify data within the lockbox that may be utilized with other portions of the SDOH repository and analytic computing entity 65. Only data for which additional access is permitted is transmitted beyond the lockbox of the SDR Tenant. Moreover, as noted data received at the SDR Tenant may be standardized into a standard file format to facilitate further analysis. Based at least in part on the standardized data formats, the SDR Tenant may consolidate and/or generate various aspects of data within the data to facilitate such further analysis. Separately (and in parallel), the SDR Tenant may intake additional data indicative of memberships of particular patients with related healthcare services to enable matching between ingested patient data and existing membership data, for example, for determining patient eligibility for various services.

The data may be provided into one more data tables, for example, comprising membership data and/or patient data thereby enabling cross-references between these data tables for additional analysis (e.g., for identifying provided data indicative of barriers to care as indicated in the patient data, and for determining whether corresponding patients are members of any healthcare services that provide eligibility-restricted access to one or more services that may address the barriers to care).

Moreover, the SDR tenant may additionally be configured for managing data of one or more service referrals, approvals, and/or the like, for example for managing audit-related reporting by the analytic computing entity 65. Moreover, certain data may be provided directly to the SDOH repository for additional storage and analysis as discussed herein.

Through the analytic computing entity 65 and/or data storage repository configurations discussed herein, and through the functionality as discussed in greater detail herein, certain embodiments are configured for distilling data from a variety of data sources, mapping that received data to various codes, and providing relevant data to various reporting systems, clinical profiles, and/or the like for reporting purposes and for generating one or more relevant referrals for services indicated as sufficient to address barriers to care identified within patient specific data.

Moreover, it should be understood that data stored within the SDOH repository may be encrypted or otherwise secured against unauthorized access, and access may be restricted to specific users and/or system ID connections. In various embodiments, the SDOH repository includes configurations for tracking access requests received and approved for audit and management purposes.

As mentioned herein, certain embodiments of the SDOH repository are configured to determine and/or store data indicative of various service characteristics corresponding to particular services that may be recommended for accommodating one or more SDOH factors of various patients. Such data may be provided or otherwise made available to the analytic computing entity prior to enabling the analytic computing entity to generate referrals and/or provide recommendations regarding such services to address SDOH factors. As just one example, the service characteristics comprise a derived standard price (DSP) corresponding to various services, thereby enabling the analytic computing entity 65 to apply a DSP to any service referral data flowing through the system, and the DSP data need not be specific to any referral source system.

As discussed herein, providing a DSP comprises mapping any incoming referral data (e.g., received via the SDH Tenant) to defined data sets of referral program types and referral program subtype proprietary codes (as discussed herein, data indicative of various services may be received via one or more external data sources and may be stored within a hierarchical data structure) stored within the SDOH repository. These propriety codes may be assigned and mapped based at least in part on referral and agency information provided from a data source. Once mapped to the referral program type and subtype, incoming referral data is assigned an appropriate DSP, with the DSP being supported by the DSP sources and having associated confidence ratings. For example, three DSP sources (certain embodiments may utilize fewer or greater than three DSP sources) for a particular referral service may be utilized to support a DSP determination for a particular referral service. These sources may comprise interactive sources (e.g., configured to receive data indicative of a usage and/or other characteristics of the referred services and to return an estimated value of the referred services based on the provided data), or informational sources (e.g., providing pricing data that may be utilized and/or input into a DSP model executed by the analytic computing entity). Moreover, these sources may be evaluated for accuracy, such as by considering various characteristics of these sources (e.g., the source type, the source date, the level of detail provided, and/or the like) to determine a confidence level to be associated with the source and/or to determine whether any adjustments should be made to the DSP data retrieved from the source (e.g., to account for inflation when considering a source that has not been updated for one or more years). As discussed herein, based at least in part on the characteristics of the source and/or the determined number of adjustments necessary based on the information in the source, the analytic computing entity determines a confidence level to be attributed to the source.

After referral data is enhanced with references to corresponding IPs (and/or other service characteristic data), all incoming referrals are enhanced with service characteristic data, with the service characteristic data being supported by one or more reference sources and confidence scores. Thereafter, all SDOH data enhancement, reporting, operational, tableau visualization, and/or clinical supporting data and/or user interfaces may be supplemented with service characteristic data such as DSP, and data may be filtered by various characteristics, such as geography, gender, program type, and/or the like.

Figure 5:
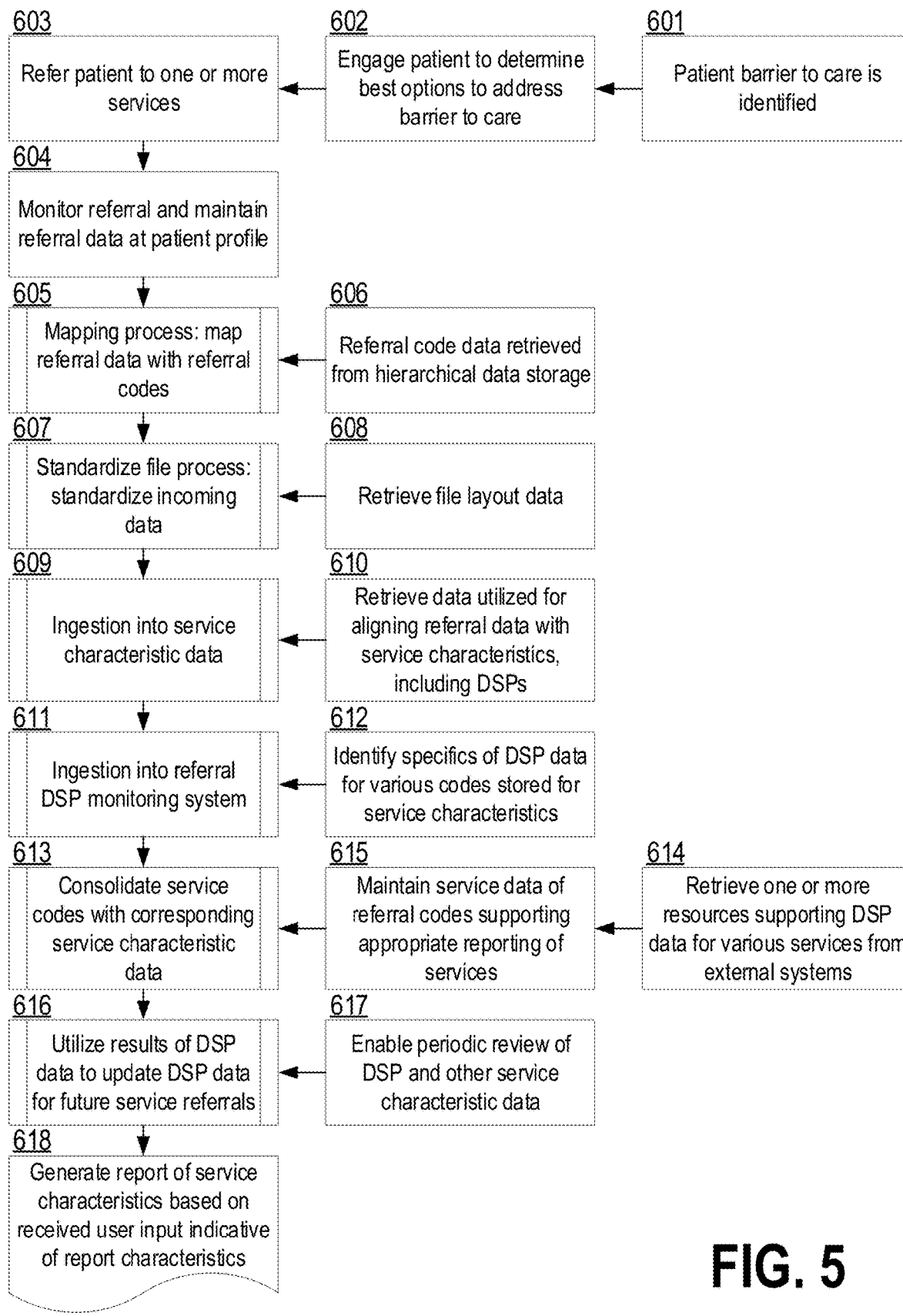
FIG. 5 is a flowchart demonstrating example functionality of various system components in accordance with certain embodiments.

FIG. 5 illustrates an example flowchart showing a process for populating data within the SDOH data storage repository. The various processes and steps reflected within the flowchart of FIG. 5 are provided in reference to an overall process for associating identified service characteristics with a referral provided to a particular user/patient. However, it should be understood that various processes as discussed herein may be performed independently of any specific referrals provided for specific patients, and data generated as a result of such processes may be utilized for associating service characteristics with service referrals of a plurality of patients over time.

With reference to FIG. 5, a patient barrier to care may be identified, as indicated at Block 601. Such patient barriers to care may be identified based at least in part on patient-provided information (e.g., information provided by a patient to a healthcare provider and input by the healthcare provider as user input to an analytic computing entity 65, for example, via a user computing entity 30). This patient-provided data may be provided in an unstructured format in certain embodiments, such as through natural-language input systems, or via structured formats (e.g., input through forms designed to elicit certain responses from the patient, such as those illustrated in the non-limiting example of FIGS. 7A-7B). As discussed in greater detail herein, patient barriers to care may be identified by specific codes to be associated with a patient profile, wherein each code is indicative of a different barrier to care for the patient. Data indicative of barriers to care may thus be received at the SDR tenant, for example, from a data source associated with the patient and/or a care provider (e.g., a user computing entity 30). The raw data received at the SDR tenant may be stored within a lockbox so as to preserve the privacy of certain patient-specific data. The SDR Tenant may be configured to generate a data file to be passed to the SDOH repository (e.g., within an appropriate data file format, such as a flat data file format as discussed herein) including data appropriate to be passed to the SDOH repository (e.g., as a part of referral data).

Moreover, it should be understood that certain additional patient-specific data may be utilized for identifying barriers to care, such as data received from one or more medical data sources (e.g., EMR data) corresponding with the patient. This additional data may similarly be stored within the lockbox of the SDR tenant in accordance with various embodiments so as to preserve the patient's privacy.

In certain embodiments, the analytic computing entity 65 (e.g., via the SDR tenant) is configured to map received patient-specific data with one or more standardized codes indicative of various barriers to care and/or SDOH factors specifically applicable to the patient. Because raw data is maintained within the SDR tenant, the SDR tenant may be configured to carry out the appropriate mapping methodology, such that the standardized codes may be passed to the SDOH repository, rather than more detailed patient-specific data so as to maintain the patient's privacy with respect to the more detailed patient-specific data.

As a part of an interaction with the patient associated with the identified barrier to care, a care provider engages the patient to determine best options for addressing the identified barrier to care (or the analytic computing entity 65 may engage the patient via a series of user interface-based questions presented to the user to ascertain a best option for addressing the barriers to care) as indicated at Block 602. This determination of a best option (and/or for identifying a plurality of potential options) for addressing the one or more barriers to care may be provided in association with the analytic computing entity 65. For example, based at least in part on patient-provided data input to the analytic computing entity 65, the analytic computing entity 65 may be configured to provide one or more recommendations of potential options for addressing identified barriers to care that a provider may discuss with the patient.

The initial intake process may continue by generating a referral for the patient to one or more services, as indicated at Block 603. The referral may reflect one or more selected services corresponding to one or more of the discussed/provided options for addressing the patient's barriers to care. The referral may correspond with a service that may have an in-person component in which a healthcare provider discusses options with the patient for how best to address the barriers to care and ultimately providing the patient with a determined best option for the patient. The referral may additionally comprise an electronic component comprising referral data comprising a request for services (to be provided to a third-party service provider computing system), wherein the request for services comprises relevant patient data (e.g., identifying data, data indicating why/how the patient qualifies for the referral services, and/or the like) that may be consolidated within a data file at the SDR Tenant and provided to the SDOH repository (and ultimately to appropriate third party service provider computing entities to initiate access to the referred services). This electronic referral data may be provided to the third-party service provider so as to enable the patient to obtain the referred services. By passing this data (e.g., within an appropriate flat file format that may be updated and/or utilized by various modules in communication with the SDOH repository) to the SDOH repository and enabling access to the data (e.g., push-related access or pull-related access) by one or more systems, the SDOH repository may be utilized for generating and/or storing patient-specific data regarding usage of referred services and/or for generating and/or storing aggregate data regarding usage of referred services, usage of more costly alternative services, and/or the like.

Ultimately, as indicated at Block 604, the referral for the patient is monitored, for example, to determine frequency of usage, costs per usage, and/or the like. As just one example, the request for services may comprise a monitoring data address, whereby a computing entity associated with the third party service provider may provide data indicative of usage of the services over time (e.g., quantity of usage episode, cost of usage episodes, and/or the like). As a specific example, for each usage of the services by a patient, the third party service provider computing entity may provide data indicative of an instance of service usage to the identified monitoring data address, thereby enabling the analytic computing entity 65 to monitor the usage of the services over time.

As a part of a monitoring process, the analytic computing entity 65 may be configured to map referral data with referral codes, thereby enabling storage of monitoring data with minimal processing resources (e.g., to match the received monitoring data with specific data indicative of usage of various services) and minimal storage resources (e.g., including a minimal amount of identifying data necessary to identify the utilized services). Such referral codes may be retrieved from storage, wherein those referral codes are provided to storage through an independently operable process, as reflected at Block 606. The service codes may be stored within an SDOH repository, as discussed above, in a hierarchical data storage configuration such as that illustrated in the example of FIG. 6.

The hierarchical data storage configuration groups various codes (and/or the corresponding services/referrals) based on determined similarities between the grouped codes. The hierarchical data storage configuration provides a plurality of levels of grouping, so as to provide highly granular comparisons between various services, referrals, and/or the like. In various embodiments, the hierarchical data structure enables comparisons in value between various services of a similar nature, so as to provide additional information regarding likely value/costs associated with providing referrals to particular services, for example, in the absence of additional information regarding the actual value attributed to a particular referred service. For example, determined similarities between referred services may be identified manually and/or automatically (e.g., via one or more machine learning models), based on characteristics such as value, geographic location, service type, typical frequency of use, and/or the like. In various embodiments, the hierarchical data may be stored within one or more data tables comprising data entries reflecting the hierarchical data storage configuration.

In various embodiments, the data stored within the hierarchical data storage configuration may be reviewed and/or updated periodically (e.g., annually, monthly, upon the occurrence of a trigger event, such as the addition of new data/codes within the hierarchical data storage configuration, and/or the like). Updating the data within the hierarchical data storage configuration may comprise updating DSP data to be utilized for determining a value to be attributed to a patient upon referring the patient to a particular service, updating grouping of data within the data storage configuration, and/or the like.

The services may be grouped into one or more service types (identifying a highest level of the hierarchical data storage configuration) and/or one or more service subtypes (identifying a second level of the hierarchical data storage configuration). With specific service subtypes, the various services may be stored therein, or such services may be stored within additional sub-hierarchical storage levels, such as another level corresponding to a service provider, and a yet-lower level corresponding to sub-types of services provided specifically by a particular service provider. In any event, services reflected within data stored at a lowest level of the data storage hierarchy reflects each of a plurality of services, together with codes (e.g., ICD-10 procedure codes or similar) reflective of the services. As discussed later herein, the service codes may be associated with various service characteristic data (e.g., derived standard price data) that may be further provided and/or utilized by an analytic computing entity 65 when determining characteristics of utilized services for a patient.

With reference to Blocks 607-608, referral data may be received from any of a plurality of data sources, such as user computing entities 30 operating at each of a plurality of healthcare provider locations. Healthcare providers may utilize any of a variety of healthcare-related software systems to provide data to the analytic computing entity 65, and accordingly the processing of received data may require the analytic computing entity 65 to standardize such received data as reflected at Blocks 607-608. As reflected at Block 608 specifically, the analytic computing entity 65 may retrieve formatting data stored within a memory storage area indicative of standardized formatting to be utilized for received data. The formatting data may be provided and stored within the memory storage area (e.g., the SDOH repository) in accordance with an independently operable data generation and storage process. In certain embodiments, the data formatting data may be accompanied with one or more APIs corresponding with particular healthcare software systems operable by various healthcare providers, such that data received from the healthcare provider software may be correlated with the standardized data formats utilized by the analytic computing entity 65. As reflected within Block 607, the analytic computing entity 65 may identify and apply applicable standardized data formats to received data.

With reference to Block 609-610, the standardized data received at the analytic computing entity 65 is ingested for further processing. Such data ingestion may occur, for example, within the SDR tenant as reflected in FIG. 4. Attributes of such data may be provided to the SDOH repository, as needed, so as to further enrich stored data (e.g., by providing data indicative of a newly available service, by providing data indicative of usage of one or more services, and/or the like). Moreover, with reference specifically to Block 610 of FIG. 5, data ingestion may comprise identifying data utilized for aligning the referral data with various service characteristics, such as by generating applicable queries to the SDOH repository to retrieve relevant service characteristic data. Such data alignment facilitates the generation of data indicative of one or more referrals of services to be provided to address and/or resolve one or more SDOH factors.

Reflected within Blocks 613-615, the analytic computing entity 65 consolidates referral data with applicable service characteristic data so as to provide a fully enriched data set utilized by the analytic computing entity for monitoring referral usage reflected by referral data for a particular patient. As indicated specifically at Block 614, the analytic computing entity 65 may store data indicative of one or more resources utilized for identifying relevant and accurate service characteristics, such as accurate identifications of derived standard pricing for various services. These resources may comprise one or more of government-provided external resources, privately provided external resources, crowd-sourced external resources, and/or the like, each of which may be accessible via corresponding resource addresses (e.g., URLs). In certain embodiments, retrieving resources supporting derived standard pricing data for various services (and/or other service characteristics) may comprise identifying a plurality (e.g., two resources, three resources, or more than three resources) of resources so as to provide support for determined derived standard pricing data, which may be reflected within a data table stored within a hierarchical data storage area. In other embodiments, retrieving a plurality of resources to provide support for derived standard pricing data may comprise retrieving derived standard pricing data directly from the one or more resources. In various embodiments, a derived standard price to be utilized for further analysis by the analytic computing entity 65 may be determined based on an average of the plurality of derived standard pricing data retrieved and stored from various resources. In certain embodiments, the average derived standard price may be a weighted average (with a higher weight associated with those sources having a higher confidence rating). In other embodiments, the derived standard pricing data to be utilized by the analytic computing entity 65 may comprise derived standard pricing data retrieved from a single resource (with other resources utilized as reference support for the identified derived standard pricing data). It should be understood that any of a variety of processes may be utilized for determining appropriate derived standard pricing to be utilized by the analytic computing entity 65. With reference again to Block 615 of FIG. 5, the analytic computing entity 65 maintains the service data in association with applicable service codes (including the derived standard pricing data to be utilized by the analytic computing entity 65 for further analysis). The stored data may be utilized by the analytic computing entity 65 to consolidate service codes with additional relevant service characteristic data for the referred services for a patient, as indicated at Block 613.

Moreover, as indicated at Blocks 616-617 of FIG. 5, the referral data specific to a particular patient (including derived standard pricing data and/or additional service characteristic data) may be utilized by the analytic computing entity 65 to update future referrals. For example, the monitored usage of services may be tracked over time to determine whether the patient utilized the referred services, and/or to determine whether the referred services were helpful in overcoming the initially identified barriers to care of the patient. In certain embodiments, patient identifying data may be removed from the resulting referral data (e.g., the monitored referral data), such that only anonymized data is utilized for customizing future referrals. Such data may be utilized as training data for a machine-learning model to identify combinations of particular barriers to care and a most-helpful service (or combination of services) to address such barriers to care. Moreover, as indicated at Block 617, various embodiments may enable periodic review of service characteristic data (e.g., including the derived standard pricing data utilized for services) so as to ensure continued relevance of the service characteristic data utilized for characterizing referred services for specific patients.

The process as reflected in FIG. 5 may ultimately generate a report of service characteristics relevant to referred patient data. The contents of the report may be standardized, or the contents of such reports may be customized, for example, based on user input received via a report-requesting user interface. In certain embodiments, the report may be presented as a portion of a patient-specific dashboard provided to a healthcare provider, for example, during a patient visit. In other embodiments, the reports may be presented as anonymized reports of the effectiveness (or other analytical characteristics) of certain services. Such example user interfaces are discussed in greater detail herein.

d. Data Intake

As discussed herein, such as in reference to Blocks 601-603, data intake in accordance with certain embodiments proceeds in accordance with user input indicative of various barriers to care relevant for specific patients. In certain embodiments, an analytic computing entity 65 is configured to provide a user interface to a user computing entity 30 to facilitate user entry of input indicative of various barriers to care. In other embodiments however, it should be understood that the user interface facilitating entry of user input indicative of barriers to care relevant for a particular user may be generated and/or provided by a separate computing entity (e.g., another healthcare-related software system executing at a healthcare provider's location). In various embodiments, the user interface (e.g., provided by the analytic computing entity 65) may provide a series of user-inquires each configured to obtain additional information regarding any barriers to care relevant to a particular patient. In other embodiments, the user interface may comprise a series of data entry fields (e.g., corresponding to a structured data storage configuration, with each of the data entry fields corresponding to a particular known data type that may be converted to standardized data by the analytic computing entity 65 for further analysis). In yet other embodiments, the user interface may be configured to receive natural language input (e.g., unstructured user input) that may be converted to standardized, structured data via one or more natural language processing configurations executing at the analytic computing entity 65.

Although discussed above specifically in reference to user input provided via a user computing entity 30 located at (and/or operated by) a healthcare provider's location, it should be understood that in certain embodiments, user interfaces may be presented directly to patients via user computing entities 30 operated by those patients, such that patients may directly provide user input indicative of various barriers to care. Moreover, it should be understood that the user input provided by a patient (and/or a healthcare provider) need not correlate directly with one or more known codes (discussed herein), as the analytic computing entity 65 may comprise one or more data mapping configurations for correlating data input received at the analytic computing entity 65 with one or more relevant codes.

In certain embodiments, additional patient data (in addition to the provided data indicative of one or more barriers to care) may be received at the analytic computing entity 65 (e.g., to the SDR Tenant) from one or more additional data sources. For example, electronic medical records (EMRs) or other electronic data indicative of various healthcare conditions of a patient may be received from one or more additional locations (e.g., EMR-storage systems). In certain embodiments, the analytic computing entity 65 as discussed herein may encompass functionality of EMR-related data storage systems (and/or the analytic computing entity 65 may be embodied as a portion of an EMR-related data storage system). In such embodiments, the analytic computing entity 65 may access patient-related data, such as existing patient profiles, to populate additional data regarding one or more patient-specified barriers to care as discussed herein.

In certain embodiments, the analytic computing entity 65 is configured to ascertain the impact of various barriers to care on the patient based at least in part on additional analysis of additional patient data accessible to and/or provided to the analytic computing entity 65. For example, the analytic computing entity 65 may be configured to determine the relative impact of various barriers to care on the patient based at least in part on additional medical conditions associated with the patient. As non-limiting examples, the analytic computing entity 65 may be configured to determine that a patient's lack of reliable transportation may have a minimal impact on the health of the patient if that patient is otherwise healthy and does not need regular transportation to various healthcare related services. However, the analytic computing entity 65 may be configured to determine that a different patient's lack of reliable transportation may have a large impact on the healthcare of the different patient based on a determination that the different patient requires regular dialysis treatment at a dedicated dialysis center and that the patient needs to travel to a pharmacy on some regular interval to obtain one or more prescription medications.

In various embodiments, at least a portion of the received patient data, such as at least the data indicative of one or more patient-specified barriers to care, may be standardized. For example, such data may be standardized into a flat data file layout accommodating input of at least three barrier data types, including an identification of a patient's barrier(s) to care, referrals to services (e.g., social services) that may assist the member with the identified barriers to care, and/or data indicative of the fulfillment of services that fully address the patient's barrier(s) to care (e.g., monitoring data indicative of usage of referred services for the patient). As data may be received from a plurality of differing data sources, each data source may be mapped to such a standardized data file format, such as via APIs generated specifically for each data source. By mapping the different data sources to the standardized file format, data provided from each data source (including terminology used by each data source, data structures utilized by each data source, and/or the like) may be mapped with established codes stored within a memory storage repository accessible to the analytic computing entity 65.

Upon generating the file having the standardized file format, the analytic computing entity 65 provides the file (e.g., upon a regular schedule) to a designated secure location for ingestion, storage, and/or provisioning to designated consumers of the data, such as in accordance with the processes discussed in reference to FIG. 5, above.

e. Data Mapping

In certain embodiments, the analytic computing entity 65 may be configured to map various patient data, including patient data indicative of one or more barriers to care, to various codes indicative of such barriers to care. Such codes may be implemented as codes developed and/or added to existing healthcare code systems, such as additional ICD-10 codes indicative of various barriers to care. Moreover, such data mapping may occur at a SDR Tenant, such that data indicative of a mapped code may be transmitted to the SDOH repository for further processing, thereby preserving more personal patient data within the privacy of the lockbox of the SDR Tenant.

In various embodiments, patient data received from various data sources, such as those data sources discussed herein, may be mapped to one or more barrier-to-care codes (e.g., a subset of ICD-10 codes, or another coding system utilized for identifying barriers to care). Such a mapping process may proceed utilizing the standardized files discussed above. Data within such standardized files may be reviewed by the analytic computing entity 65 (e.g., by reviewing specific structured data therein, by reviewing partially structured data, for example, with natural language processing configurations, and/or the like) to identify data indicative of one or more barriers to care. As an example, the analytic computing entity 65 may identify barriers to care based on combinations of user-provided answers to various user-prompts (e.g., user-prompts being designed to elicit data indicative of difficulties of the patient in obtaining necessary healthcare services). Upon identifying such barriers of care, the analytic computing entity 65 may assign relevant codes indicative of such identified barriers to care. As another example, the analytic computing entity 65 may identify barriers to care within unstructured (or partially structured) data via one or more of natural language processing configurations, specific word/phrase identification systems, and/or the like. Based on identified barriers to care identified within the unstructured/partially-structured data, the analytic computing entity 65 may associate one or more barrier-to-care codes with the patient data reflected within the provided data file.

Such codes may be utilized in combination with existing codes, for example, to ascertain the level of impact that a particular barrier to care has on a particular patient, based at least in part on additional codes (e.g., diagnostic codes) associated with the patient. In various embodiments, the analytic computing entity 65 may be configured to utilize a machine-learning based model for determining the level of impact that a particular barrier of care has on a patient. Such a machine-learning based model may utilize historical data (e.g., anonymized historical data) indicative of particular diagnostic codes and barrier-to-care codes (indicative of barriers to care of a patient), as well as services provided and ultimate healthcare outcomes associated with the historical patients to determine a level of impact of a barrier to care on the healthcare of a patient. It should be understood that such machine-learning based models may be trained in accordance with any of a variety of training methodologies, including supervised learning, unsupervised learning, and/or the like.

f. Identification of Service Recommendations and Data Transfer

As discussed herein, the analytic computing entity 65 may be configured to identify one or more relevant services for addressing identified barriers to care relevant to a particular patient. Such services may comprise one or more government or publicly provided services, such as social programs, subsidy programs, and/or the like. In other embodiments, the services may comprise one or more privately-provided services, such as services provided by one or more healthcare payers (e.g., healthcare insurance providers). Data reflecting each of the available services may be stored within a data storage repository accessible to the analytic computing entity 65. As just one example, data reflecting each of the available services may be stored within service profiles each corresponding to a particular available service. The service data reflected within particular service profiles (or otherwise indicative of characteristics of various services) may comprise an identification of a service provider, a description of the service, data identifying one or more barriers to care codes that may be addressed by the particular service, data indicative of a service category (e.g., for storing the data within a hierarchical data storage repository as discussed herein), data identifying one or more qualifications for patients to qualify for such services (e.g., income thresholds, required memberships, and/or the like), and/or the like. Moreover, as discussed above, the service profiles (or other data indicative of characteristics of various services) may comprise one or more references (e.g., links to external data sources) to support the various included data indicative of characteristics of the service, including, for example, data supporting a derived standard price to be attributed to the service.

As discussed herein, service profiles corresponding to individual services available for addressing various barriers to care are stored within a hierarchical data storage repository. These service profiles may each be populated at least in part based on manual user input, as new services become available, or automatically (e.g., as new services become available within a linked service repository, for example, of a service provider).

The hierarchical data structure enables analysis based at least in part on various data types, service types, and/or the like. For example, the hierarchical data structure may be organized such that services of a common service type are organized together, and services provided by a single service provider (and of the same service type) may likewise be organized together. Utilizing this hierarchical data structure, analysis of the effectiveness, efficiency, and/or the like of services within a single service type structure, and/or services provided by a single service provider (and of a single service type) may be performed collectively.

Figure 6:
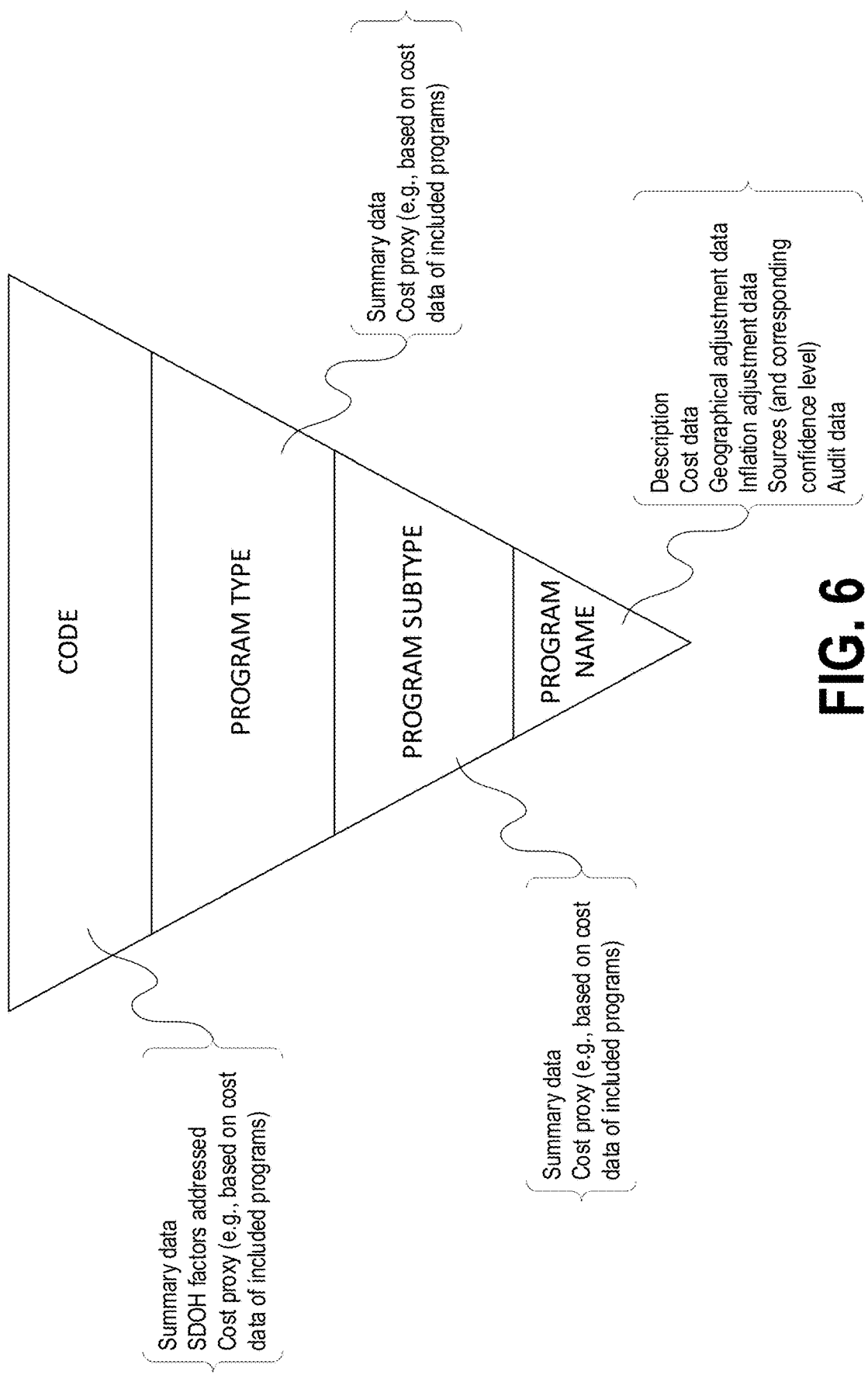
FIG. 6 illustrates an example hierarchical data storage strategy for storing characteristic data of various services in accordance with certain embodiments.
Figure 8:
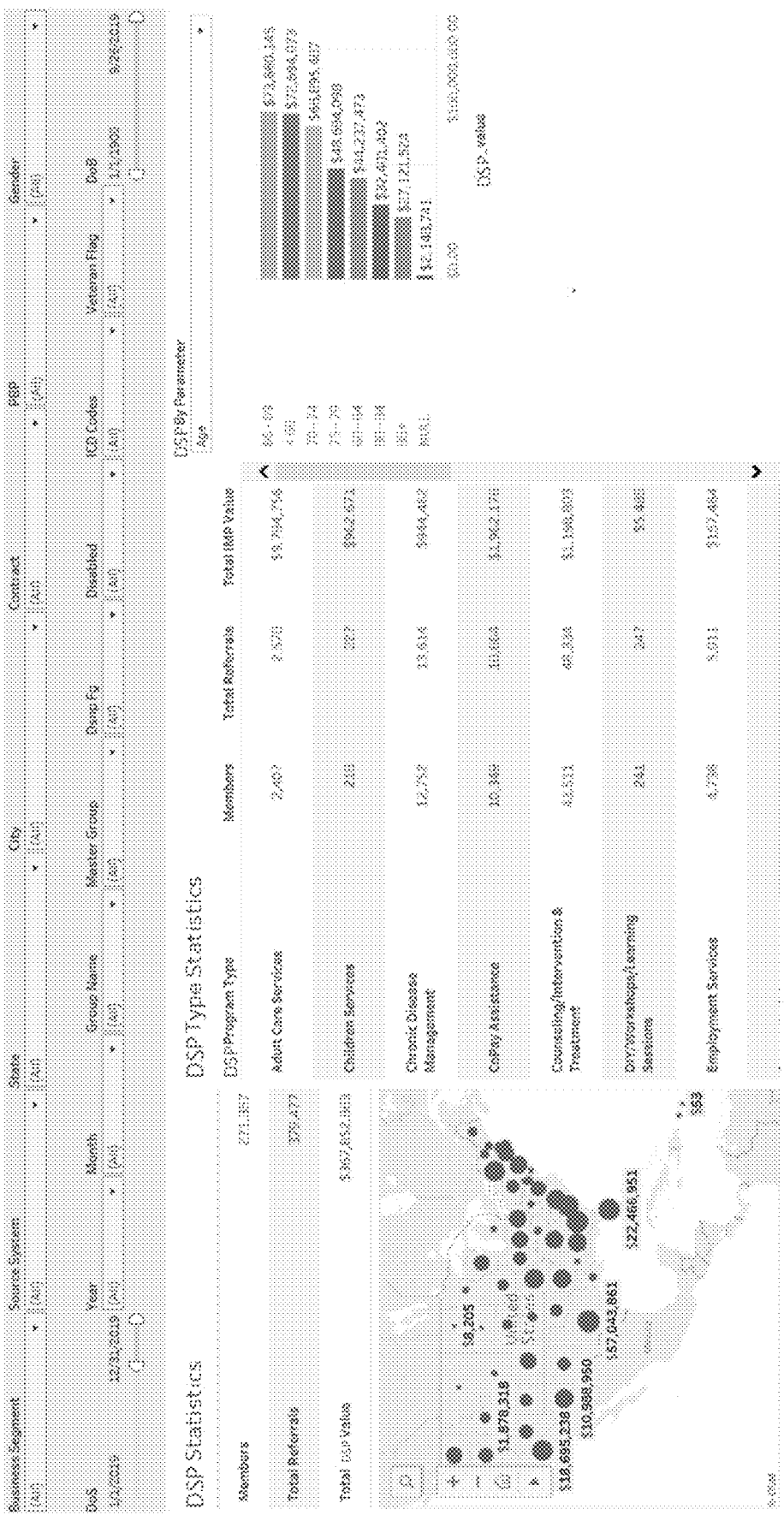
FIGS. 8-12 illustrate example user interfaces in accordance with certain embodiments.

FIG. 6 illustrates an example hierarchical structure that may be utilized for storing service profiles in accordance with certain embodiments. For example, a highest-level (broadest level) of a hierarchical data structure may be embodied as a ZCODE (or other code). The code may be embodied as a diagnostic code corresponding to barriers to care that services stored thereunder may address (e.g., ICD-10 codes), a procedure code, and/or the like. Particularly for embodiments in which the highest level of the hierarchical data storage repository is reflected by a diagnostic code corresponding to particular barriers to care, such data may be utilized to easily identify services available for addressing particular barriers to care applicable to a patient. Moreover, in those embodiments in which data is stored in a data table comprising data identifying the various hierarchical data, it should be understood that data indicative of the highest level within the hierarchical structure may be reflected by a data entry within a data storage table for a particular service.

A second level of the hierarchical data storage repository may identify service types (e.g., transportation services) to which the included service profiles relates. These service types may be identified manually or automatically in certain embodiments. Similarly, in certain embodiments a third level of a hierarchical data storage repository may identify a service subtype (e.g., senior & disabled ride services). Again, such subtype classification may be applied to specific services manually or automatically in certain embodiments. It should be understood that additional subcategories may be provided in certain embodiments. Moreover, as discussed above, the second (and/or other) levels of categorization reflected within the hierarchical data storage structure may be reflected as data entries provided for particular services.

Each service profile may correspond to one of each of a plurality of hierarchical data storage levels within a defined taxonomy of services. The taxonomy of services may be established at least in part based on manual user input identifying particular codes, service types, service subtypes, and/or the like. In other embodiments, the taxonomy of services may be established at least in part based on automated modelling, for example using a machine-learning based clustering model to generate clusters of related services, and to provide labels for each generated cluster corresponding to various service types and/or service subtypes. For example, metadata assigned to each service profile may identify a corresponding highest hierarchical data storage level (e.g., a code), a second hierarchical data storage level (e.g., a service type), a third hierarchical data storage level (e.g., a service subtype), and/or the like. As mentioned, such a structure enables an analysis at any level of the hierarchical data storage repository, for example, to determine the average cost to address a particular code (e.g., a diagnostic code, if utilized as a highest level of the hierarchical data storage repository), the average cost to implement a particular service type (e.g., the average cost of all services within a transportation service type), the average cost to implement a particular service subtype (e.g., the average cost of senior & disabled ride services), and/or the like. Specifically, cost data (reflective of a value provided to a user/patient) may be provided for each service as reflected within the hierarchical data storage structure. Moreover, in certain embodiments, entries for particular services may comprise additional data indicative of potential adjustments that may be applied to the provided cost data, such as geographical cost adjustments, inflation-based cost adjustments, and/or the like. Such entries may be utilized for determining an accurate value estimate for patients based on specific characteristics of those patients and the circumstances under which a referral to the particular service is provided. Moreover, because each service is associated with higher-level categorizations within the hierarchical data storage structure, the cost data may be utilized to determine estimated average costs across an entire category (e.g., an entire top-level category, an entire second-level category, and/or the like). For example, cost data for each service associated with a particular category may be analyzed (e.g., to determine an average overall cost) that may be utilized for determinations of an average overall cost across all services within a particular category.

Moreover, the service profiles may each comprise service characteristics data indicative of characteristics of a corresponding service. Such service characteristic data may comprise eligibility criteria (e.g., identifying one or more factors of a patient considered to determine whether the patient is eligible for the service), data indicative of availability of the service (e.g., geographical limits of the service, time-limits of the service (e.g., daily availability by time), quantity availability of the service (e.g., number of services available per day), and/or the like), data indicative of costs associated with the service, and/or the like. Such service characteristic data may be supported by one or more resources that may be identified and/or linked with a corresponding service profile. The resources may comprise Internet-accessible resources, such as websites, webpages, and/or the like, that provide information regarding various characteristics of a service corresponding to the linked service profile. In certain embodiments, the resources may be government provided resources (e.g., corresponding to government provided services), privately provided resources (e.g., corresponding to privately provided services), crowd-sourced resources, and/or the like. In certain embodiments, a plurality of resources may be associated with a particular service profile, thereby providing multiple indications of characteristics of the corresponding services. Particularly for those resources providing data indicative of a derived standard price to be attributed to the service, the analytic computing entity 65 may be configured to determine a derived standard price utilizing one of a plurality of methodologies. For example, the analytic computing entity 65 may be configured to generate an average derived standard price based at least in part on pricing data provided by each of the resources. In other embodiments, the analytic computing entity 65 may be configured to select pricing data provided by a single resource to generate a derived standard pricing model for a service. As an example, the analytic computing entity 65 may be configured to select a resource deemed most relevant (e.g., utilizing rule-based selection criteria, such as a relevance hierarchy, establishing that government-provided resources are considered most relevant, if available, then privately-provided resources, and finally crowd-sourced resources being considered least relevant), and to utilize the most-relevant available resource for establishing the derived standard price for the service. The unused resources may remain linked with the service profile, and may be referenced for additional support for establishing various characteristics of the corresponding service.

Although discussed above specifically in providing data characteristics specific to one or more services, in certain embodiments the hierarchical data storage repository may comprise data indicative of one or more characteristics for a service type, a service subtype, or any other level within the hierarchical data storage repository. In certain embodiments, data characteristics applicable to particular service subtypes may identify corresponding program types (e.g., a higher level within the hierarchical data storage repository), a general description of services within the service subtype, a derived standard price for the service subtype, a confidence level corresponding to the derived standard price (e.g., determined based at least in part on one or more characteristics of resources utilized to establish the derived standard price), as well as additional detail regarding the service subtype and/or data indicative of a most-recent review of the included data.

In certain embodiments, a confidence rating for a particular derived standard price may be established based at least in part on one or more characteristics utilized for establishing the derived standard price. In certain embodiments, the confidence level may be established utilizing one or more rule-based configurations or machine-learning based configurations. As just one example, a confidence level may be established based at least in part on a source from which the derived standard pricing data is retrieved. As discussed herein particularly in reference to establishing a derived standard price for a particular service, the analytic computing entity 65 may identify preferred resources for providing data indicative of derived standard pricing. Accordingly, receiving data utilized for establishing a derived standard price from a more-preferred resource type may correlate to a higher confidence level for the determined derived standard price. As another example, a confidence level for a derived standard price may be determined based at least in part on a determined standard deviation (or other evaluation of differences in derived standard price values) of derived standard price values obtained from a plurality of resources corresponding to the service (or service subtype or service type). A smaller distribution of derived standard price values (indicative of a higher level of consistency in derived standard price values obtained from a plurality of sources) may correlate to a higher confidence level for the derived standard pricing data provided. As yet another example, a confidence level may be determined based at least in part on the recency with which a particular resource has been updated, such that more recently updated resources may be provided with a higher confidence level. It should be understood that in certain embodiments, a plurality of factors may be considered simultaneously to determine a most-relevant confidence level for a particular resource. It should be understood that while such confidence levels are described herein with respect to providing a derived standard price for a service type or service subtype, it should be understood that similar configurations may be utilized for establishing a confidence level for specific services.

Utilizing the hierarchical data structure, a recommended service for addressing a particular patient's barriers to care may be identified and recommended for the patient. As mentioned, barriers to care may be identified for a patient and represented as a code within a patient profile (e.g., a diagnostic code corresponding to the barrier to care). The code may be automatically identified as a code representative of a barrier to care, or the code may be manually identified as a code representative of a barrier to care for which one or more services should be reviewed to address the barrier to care. In various embodiments, whether through automated configurations or manual initiation, the analytic computing entity is configured to query the hierarchical data storage repository based at least in part on the code identified for the patient's barrier to care to identify one or more service types, service subtypes, and/or specific programs identified as addressing a barrier to care having the queried code. In certain embodiments, particularly where there are a plurality of options of services for addressing a barrier to care, the analytic computing entity 65 may be configured to present a plurality of options for selection by the patient and/or the patient's care provider for selection of a most-appropriate option of a service for the patient. In other embodiments, the analytic computing entity 65 may be configured to automatically select a particular service (e.g., based on popularity of selections of services, based on one or more characteristics of the service, such as cost, ease-of-use, and/or the like, as reflected within data indicative of characteristics of the service, and/or the like). Such automated selections may be performed by the analytic computing entity 65 based at least in part on rule-based selection criteria, or artificial intelligence based models (e.g., trained via one or more training data sets).

Moreover, the analytic computing entity 65 may be configured to perform one or more eligibility checks for particular services to determine whether a patient qualifies for the services, and/or whether the services are offered to the patient (e.g., based on geographical limitations). Data indicative of service characteristics stored within service profiles may comprise data indicating eligibility criteria, geographical availability, and/or the like for corresponding services. When determining whether a particular patient may utilize an identified service to address a known barrier to care, the analytic computing entity may be configured to compare patient characteristics (e.g., as reflected within patient data stored within a patient profile) against service characteristics (e.g., reflected within service characteristic data stored within a service profile) to determine whether the service is available to the patient and/or whether the patient is eligible for the service. Only those services deemed available to the patient and for which the patient is eligible may be determined and/or considered for use in addressing the patient's barrier to care. As noted above, if a plurality of services are identified as available to the patient and for which the patient is deemed eligible, one or more automated and/or manual processes may be utilized for selecting one or more services to address the patient's barrier to care.

g. Example User Interfaces

FIGS. 8-12 illustrate example user interfaces that may be generated at least in part utilizing data of certain embodiments as discussed herein. Such user interfaces may reflect example reports/dashboards that may be generated for analyzing the prevalence of various barriers to care and/or other SDOHs, for illustrating various barriers to care and/or SDOHs applicable to a particular patient (e.g., which may be presented as a part of a larger patient clinical profile), and/or the like.

Figure 10:
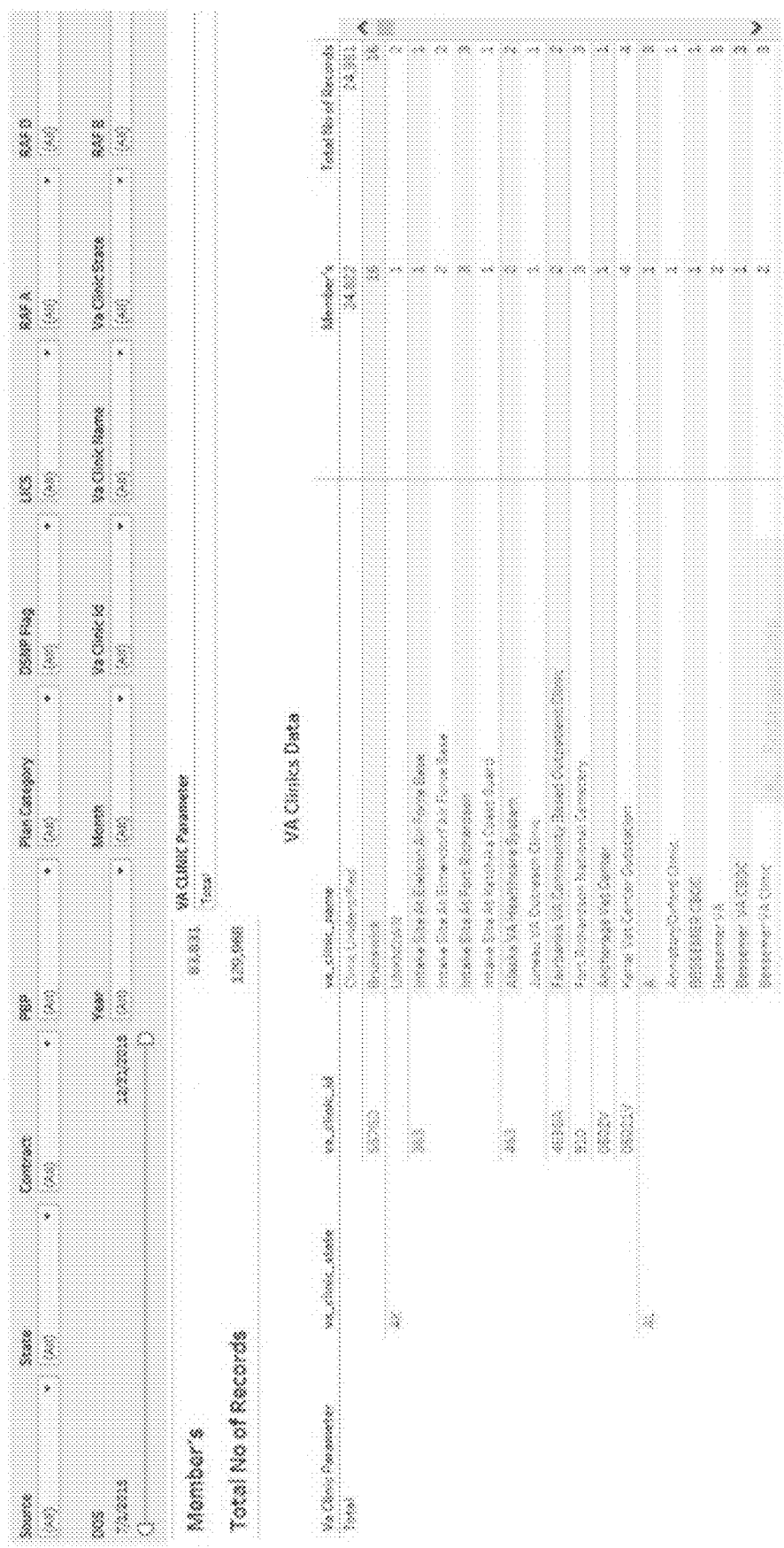

As just one example, FIG. 10 illustrates an example report illustrating data indicative of the prevalence of various SDOHs (e.g., identified based at least in part on codes generated and indicative of various barriers to care as identified by patients), as well as data indicating a derived standard price attributed to services referred for addressing each SDOH. Because such data may be associated with patient data (e.g., patient profile data, including, for example, geographic location data), the provided data for a plurality of patients may be anonymized and reported within a graphical user interface displaying relevant information arranged by geographic location (e.g., within a displayed map), displaying relevant information organized based on other characteristics (e.g., organized based at least in part on SDOH code), and/or the like. Moreover, as evident in the example graphical user interface of FIG. 8, the display may comprise a plurality of user-selectable filters and/or display options for further customizing the displayed data, as desired by a user.

Figure 9:
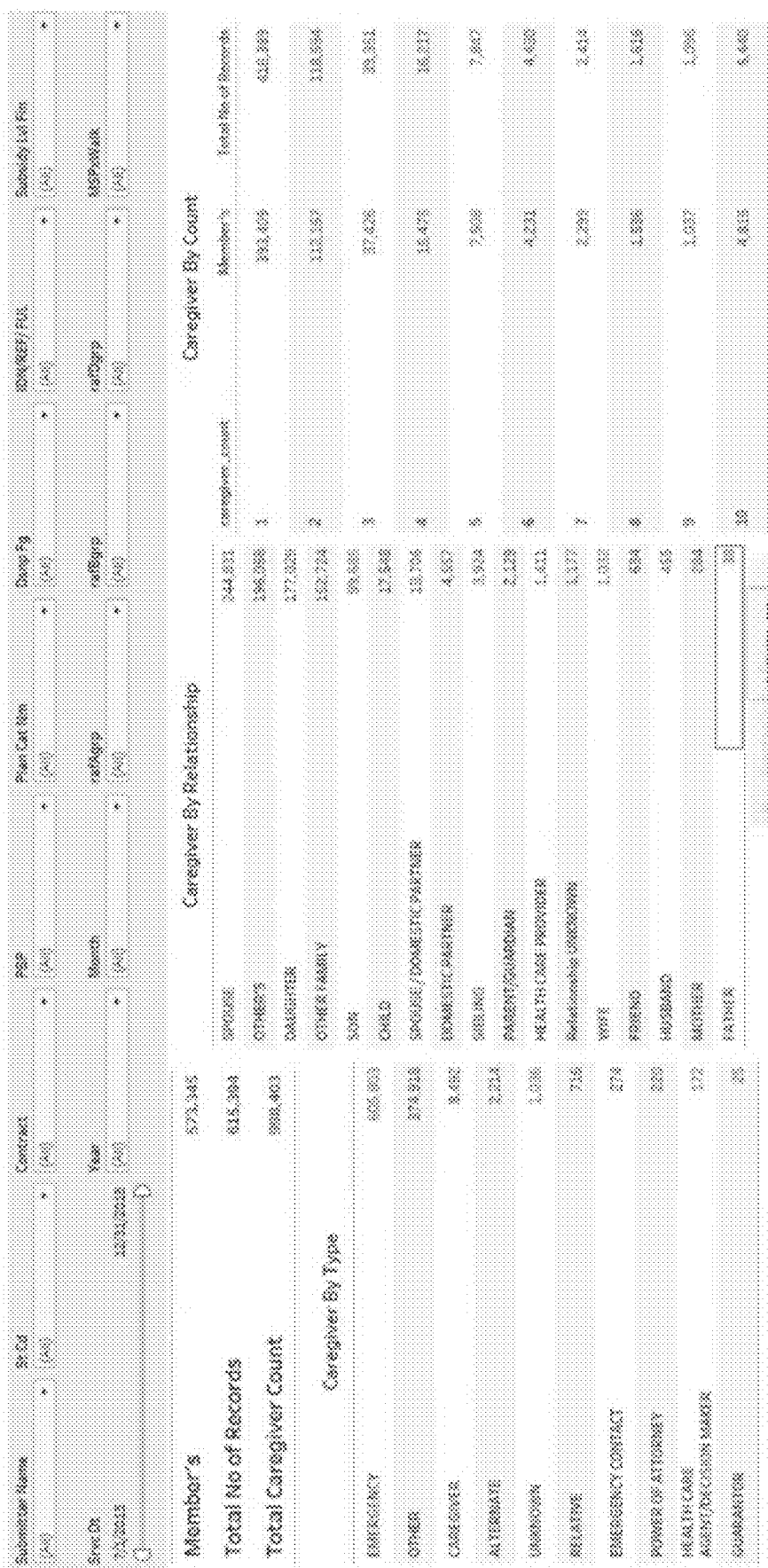

FIG. 9 provides another example user interface providing a reporting functionality in accordance with one embodiment. As displayed therein, the graphically displayed reporting user interface may provide anonymized data indicative of various characteristics of patients reflected within the data, which may be organized based at least in part on a caregiver type.

FIG. 10 provides yet another example reporting-related graphical user interface, specifically providing data indicative of various patients having data indicating that the patient is a veteran. Such data may be presented in an anonymized fashion to present data indicative of the number of veterans reflected within the data and being associated with various healthcare facilities.

Figure 11:
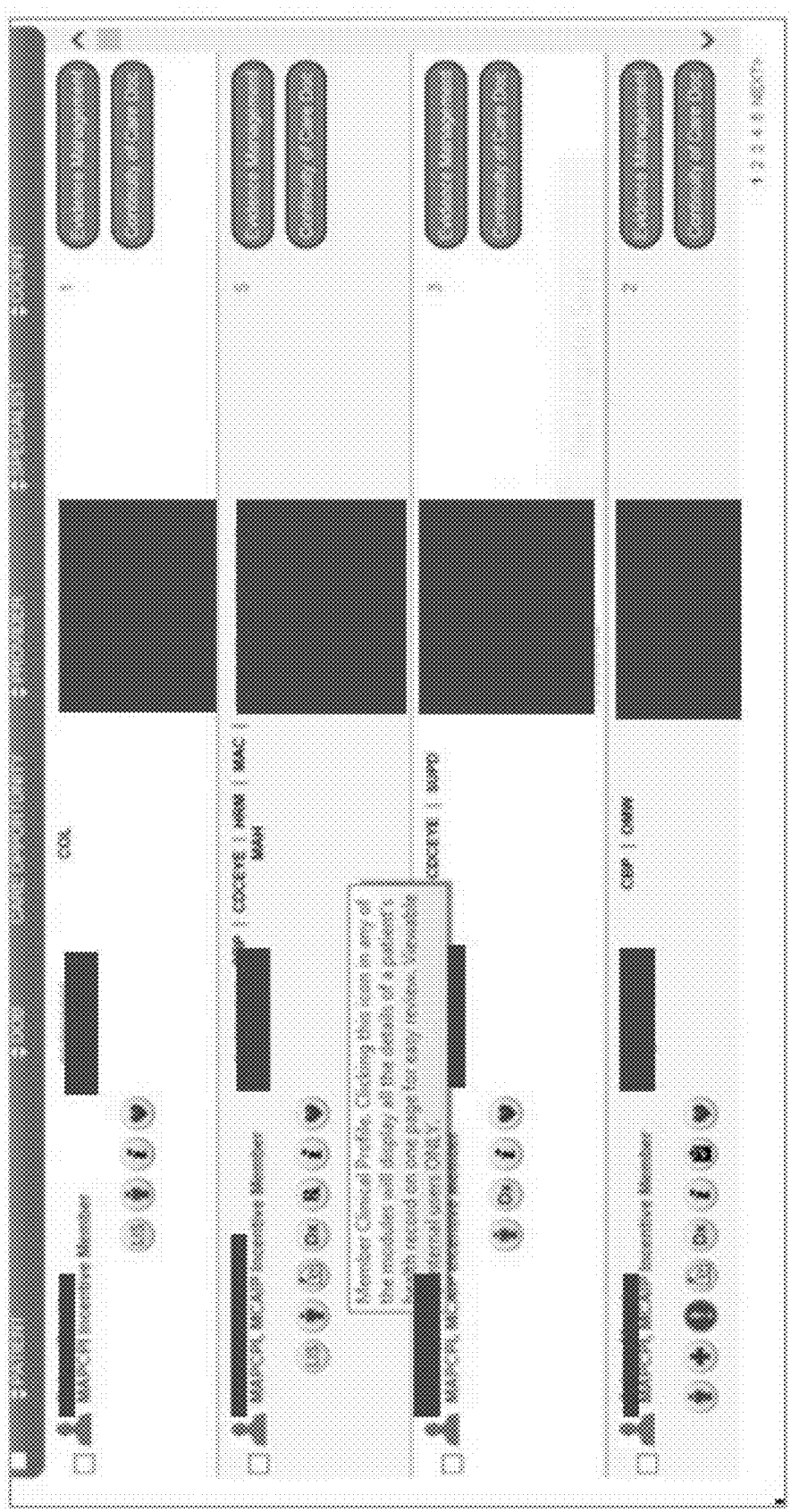
Figure 12:
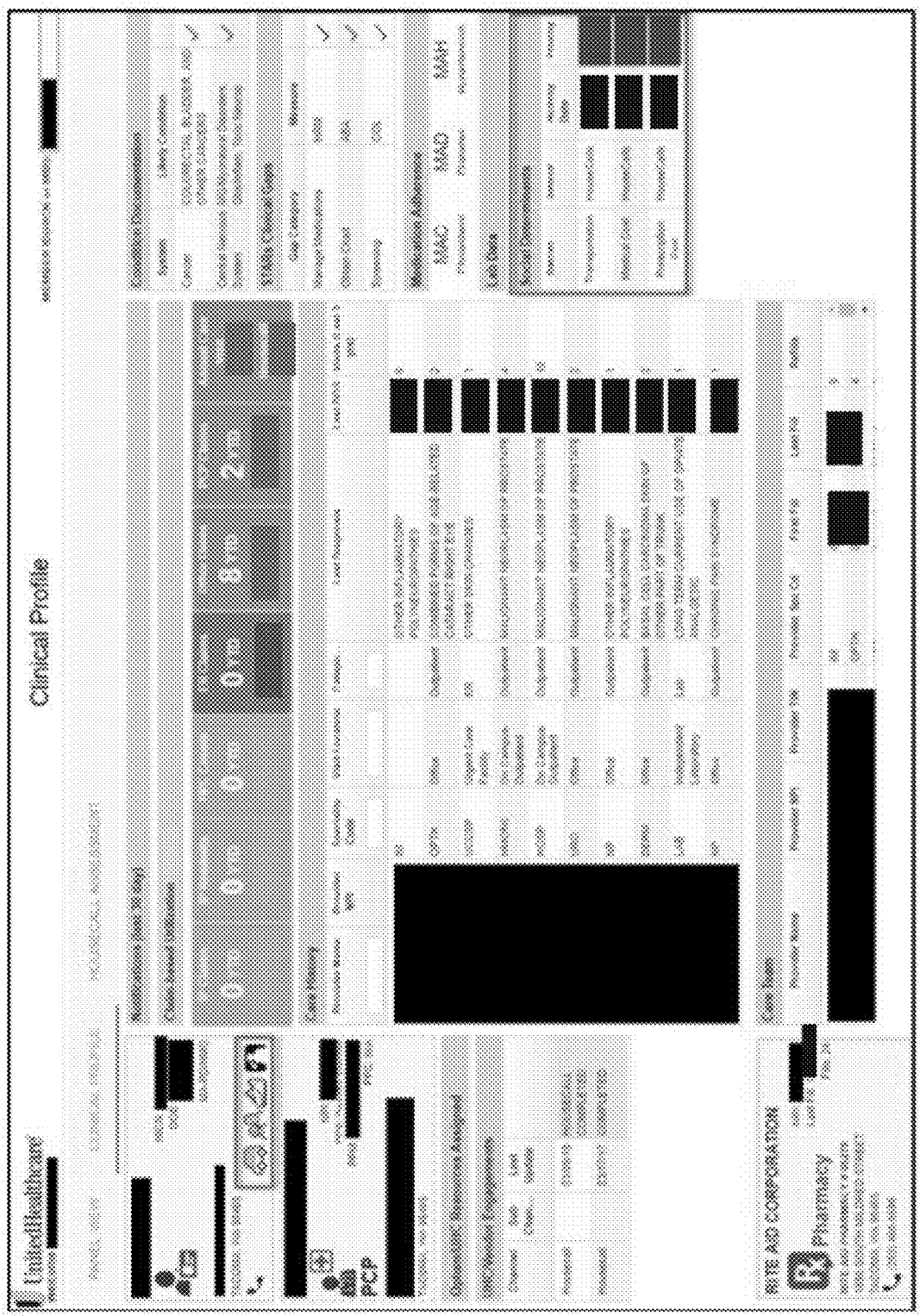

FIG. 11 provides another example user interface in accordance with certain embodiments. Specifically, FIG. 11 illustrates an example display through which a user of the analytic computing entity 65 (e.g., via one or more user computing entities 30) may select a particular patient to obtain additional, patient specific data, such as accessing a patient profile/dashboard, an example of which is shown at FIG. 12. As shown therein, the patient profile may comprise identifying data of the patient, data indicative of one or more care providers of the patient, data indicative of care history of the patient, data indicative of various SDOH factors associated with the patient, and/or the like. Such data may be updated in accordance with the systems and methods as discussed herein, thereby providing healthcare providers of the patient with updated data indicative of various applicable SDOH factors of the patient, such that the healthcare provider may tailor treatment options (if applicable) to the patient's applicable SDOH factors.

IV. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented method comprising:
   receiving, by one or more processors associated with a secure data repository operating as a discrete repository tenant within a memory of a computing system, input indicative of a plurality of Social Determinant of Health (SDOH) factors for a patient;
   generating, by the one or more processors, SDOH factor data indicative of the plurality of SDOH factors;
   receiving, by the one or more processors, patient data from a patient profile corresponding to the patient;
   standardizing, by the one or more processors, the SDOH factor data by mapping at least a portion of the SDOH factor data to one or more codes identified within a code-base repository stored in the secure data repository to generate a flat data file comprising one or more standardized codes for the patient;
   integrating, by the one or more processors, the one or more standardized codes into the patient data for storage within a data table of the secure data repository;
   identifying, by the one or more processors, one or more accessible data elements stored within the secure data repository for transfer to a separate SDOH repository, wherein the one or more accessible data elements comprise at least a first portion of the patient data and at least one of the one or more standardized codes;
   transferring, by the one or more processors, the one or more accessible data elements from the secure data repository to the separate SDOH repository within the memory, wherein the separate SDOH repository is isolated from the secure data repository such that the patient data and the one or more standardized codes stored within the secure data repository are isolated from and inaccessible to external interfaces between the memory and one or more authorized external service provider computing systems;
   based at least in part on the one or more standardized codes integrated into the patient data, identifying, by the one or more processors, one or more recommended external service provider computing systems of the one or more authorized external service provider computing systems for one or more electronically-provided services;
   transmitting, by the one or more processors and from the separate SDOH repository, at least a second portion of the patient data to a subset of the one or more recommended external service provider computing systems to initiate the one or more electronically-provided services;
   querying, by the one or more processors, a hierarchical data structure comprising characteristic data corresponding to each of the one or more electronically-provided services, wherein the characteristic data is determined based at least in part from one or more supporting resources linked with the hierarchical data structure;
   populating, by the one or more processors and in the separate SDOH repository, a third portion of the patient data selected from the first portion with the one or more standardized codes and at least a portion of the characteristic data; and
   generating, by the one or more processors and in association with the separate SDOH repository, a visual patient profile dashboard comprising at least the third portion of the patient data.

2. The computer-implemented method of claim 1, wherein transmitting the second portion of the patient data to the subset of the one or more recommended external service provider computing systems comprises:
   detecting a trigger event indicative of a need for the one or more electronically-provided services provided by the subset of the one or more recommended external service provider computing systems; and
   upon detecting the trigger event, transmitting the second portion of the patient data to the subset of the one or more recommended external service provider computing systems to initiate the one or more electronically-provided services.

3. The computer-implemented method of claim 2, further comprising:
   monitoring usage of the one or more electronically-provided services based at least in part on a monitored frequency of trigger events.

4. The computer-implemented method of claim 3, further comprising populating the third portion of the patient data with usage data indicative of usage of the one or more electronically-provided services.

5. The computer-implemented method of claim 4, wherein the usage data comprises an annualized cost determined based at least in part on a monitored usage of the one or more electronically-provided services and the characteristic data corresponding to the one or more electronically-provided services.

6. The computer-implemented method of claim 1, further comprising:
   prior to transferring the one or more accessible data elements to the SDOH repository, anonymizing, at the secure data repository, at least a portion of the one or more accessible data elements comprising the one or more standardized codes to generate anonymized patient data for a plurality of patients, wherein the plurality of patients comprises the patient;

consolidating the anonymized patient data for a plurality of patients via the SDOH repository; and generating one or more SDOH reports comprising the anonymized patient data for the plurality of patients.

7. The computer-implemented method of claim 1, wherein the hierarchical data structure comprises a first data storage level identifying a plurality of service types and a second data storage level within each of a plurality of instances of the first data storage level, wherein the second data storage level identifies the one or more electronically-provided services and the characteristic data corresponding to the one or more electronically-provided services.

8. A system comprising:
one or more memory storage repositories comprising a secure data repository and a Social Determinant of Health (SDOH) repository operating as a discrete repository tenant, wherein the SDOH repository (a) is accessible by one or more authorized external service provider computing systems and (b) the secure data repository is isolated from the one or more authorized external service provider computing systems such that patient data and one or more standardized codes stored within the secure data repository are isolated from and inaccessible to the one or more authorized external service provider computing systems, and wherein the secure data repository is configured for transferring at least a portion of the data and at least a portion of the one or more standardized codes to the SDOH repository via a data transfer interface executable with one or more processors;

the one or more processors are configured to independently access the patient data and the one or more standardized codes within one of the secure data repository and the SDOH repository, wherein the one or more processors are configured to:

receive input indicative of a plurality of SDOH factors for a patient;

store the input indicative of the plurality of SDOH factors for the patient within the secure data repository;

generate SDOH factor data indicative of the plurality of SDOH factors within the secure data repository;

receive patient data from a patient profile corresponding to the patient;

standardize the SDOH factor data by mapping at least a portion of the SDOH factor data to one or more codes identified within a code-base repository stored in the secure data repository to generate a flat data file comprising one or more standardized codes for the patient;

integrate the one or more standardized codes into the patient data for storage within a data table of the secure data repository;

identify one or more accessible data elements stored within the secure data repository for transfer to the SDOH repository, wherein the one or more accessible data elements comprise at least a first portion of the patient data and at least one of the one or more standardized codes;

transfer at least a portion of the patient data and the one or more standardized codes from the secure data repository to the SDOH repository;

based at least in part on the one or more standardized codes integrated into the patient data, identify one or more recommended external service provider computing systems of the one or more authorized external service provider computing systems for one or more electronically-provided services;

transmit, from the SDOH repository, at least a second portion of the patient data to a subset of the one or more recommended external service provider computing systems to initiate the one or more electronically-provided services;

query a hierarchical data structure comprising characteristic data corresponding to each of the one or more electronically-provided services, wherein the characteristic data is determined based at least in part from one or more supporting resources linked with the hierarchical data structure;

populate, in the SDOH repository, a third portion of the patient data selected from the first portion with the one or more standardized codes and at least a portion of the characteristic data; and generate, in association with the SDOH repository, a visual patient profile dashboard comprising at least the third portion of the patient profile.

9. The system of claim 8, wherein transmitting the second portion of the patient data to the subset of the one or more recommended external service provider computing systems comprises:

detecting a trigger event indicative of a need for the one or more electronically-provided services provided by the subset of the one or more recommended external service provider computing systems; and upon detecting the trigger event, transmitting the second portion of the patient data to the subset of the one or more recommended external service provider computing systems to initiate the one or more electronically-provided services.

10. The system of claim 9, wherein the one or more processors are further configured to:

monitor usage of the one or more electronically-provided services based at least in part on a monitored frequency of trigger events.

11. The system of claim 10, wherein the one or more processors are further configured to populate the third portion of the patient data with usage data indicative of usage of the one or more electronically-provided services.

12. The system of claim 11, wherein the usage data comprises an annualized cost determined based at least in part on a monitored usage of the one or more electronically-provided services and the characteristic data corresponding to the one or more electronically-provided services.

13. The system of claim 8, wherein the one or more processors are further configured to:

prior to transferring the one or more accessible data elements to the SDOH repository, anonymize, at the secure data repository, at least a portion of the one or more accessible data elements comprising the one or more standardized codes to generate anonymized patient data for a plurality of patients, wherein the plurality of patients comprises the patient;

consolidate the anonymized patient data for a plurality of patients via the SDOH repository; and generate one or more SDOH reports comprising the anonymized patient data for the plurality of patients.

14. The system of claim 8, wherein the hierarchical data structure comprises a first data storage level identifying a plurality of service types and a second data storage level within each of a plurality of instances of the first data storage level, wherein the second data storage level identifies the one or more electronically-provided services and the characteristic data corresponding to the one or more electronically-provided services.

15. A computer program product comprising a non-transitory computer readable medium having computer program instructions stored therein, the computer program instructions when executed by a processor, cause the processor to:
receive input indicative of social determinants of health (SDOH) factors for a patient at a secure data repository operating as a discrete repository tenant within a memory of a computing system;
store the input indicative of the plurality of SDOH factors for the patient within the secure data repository;
generate SDOH factor data indicative of the plurality of SDOH factors in association with the secure data repository;
receive patient data from a patient profile corresponding to the patient;
standardize the SDOH factor data by mapping at least a portion of the SDOH factor data to one or more codes identified within a code-base repository stored in the secure data repository to generate a flat data file comprising one or more standardized codes for the patient;
integrate the one or more standardized codes into the patient data for storage within a data table of the secure data repository;
identify one or more accessible data elements stored within the secure data repository for transfer to a separate SDOH repository, wherein the one or more accessible data elements comprise at least a first portion of the patient data and at least one of the one or more standardized codes;
transfer the one or more accessible data elements from the secure data repository to the separate SDOH repository within the memory, wherein the separate SDOH repository is isolated from the secure data repository such that the patient data and the one or more standardized codes stored within the secure data repository are isolated from and inaccessible to external interfaces between the memory and one or more authorized external service provider computing systems;
based at least in part on the one or more standardized codes integrated into the patient data, identify one or more recommended external service provider computing systems of the one or more authorized external service provider computing systems for one or more electronically-provided services;
transmit, from the separate SDOH repository, at least a second portion of the patient data to a subset of the one or more recommended external service provider computing systems to initiate the one or more electronically-provided services;
query a hierarchical data structure comprising characteristic data corresponding to each of the one or more electronically-provided services, wherein the characteristic data is determined based at least in part from one or more supporting resources linked with the hierarchical data structure;
populate, in the separate SDOH repository, a third portion of the patient data selected from the first portion with the one or more standardized codes and at least a portion of the characteristic data; and
generate, in association with the separate SDOH repository, a visual patient profile dashboard comprising at least the third portion of the patient data.

16. The computer program product of claim 15, wherein transmitting the second portion of the patient data to the subset of the one or more recommended external service provider computing systems comprises:
detecting a trigger event indicative of a need for the one or more electronically-provided services provided by the subset of the one or more recommended external service provider computing systems; and
upon detecting the trigger event, transmitting the second portion of the patient data to the subset of the one or more recommended external service provider computing systems to initiate the one or more electronically-provided services.

17. The computer program product of claim 16, wherein the computer program instructions when executed by a processor, cause the processor to further:
monitor usage of the one or more electronically-provided services based at least in part on a monitored frequency of trigger events.

18. The computer program product of claim 17, wherein the usage data comprises an annualized cost determined based at least in part on a monitored usage of the one or more electronically-provided services and the characteristic data corresponding to the one or more electronically-provided services.

19. The computer program product of claim 15, wherein the computer program instructions when executed by a processor, cause the processor to further:
prior to transferring the one or more accessible data elements to the SDOH repository, anonymize, at the secure data repository, at least a portion of the one or more accessible data elements comprising the one or more standardized codes to generate anonymized patient data for a plurality of patients, wherein the plurality of patients comprises the patient;
consolidate the anonymized patient data for a plurality of patients via the SDOH repository; and
generate one or more SDOH reports comprising the anonymized patient data for the plurality of patients.

20. The computer program product of claim 15, wherein the hierarchical data structure comprises a first data storage level identifying a plurality of service types and a second data storage level within each of a plurality of instances of the first data storage level, wherein the second data storage level identifies the one or more electronically-provided services and the characteristic data corresponding to the one or more electronically-provided services.

* * * * *